United States Patent
Genet et al.

(10) Patent No.: US 6,419,711 B1
(45) Date of Patent: Jul. 16, 2002

(54) OXIDATION DYEING COMPOSITIONS CONTAINING A CATIONIC COUPLING AGENT, NOVEL CATIONIC COUPLING AGENTS

(75) Inventors: Alain Genet, Aulnay-sous-Bois; Alain Lagrange, Coupvray, both of (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 09/646,455

(22) Filed: Nov. 13, 2000

(30) Foreign Application Priority Data

Mar. 20, 1998 (FR) .............................. 98 03455

(51) Int. Cl.⁷ ................................ A61K 7/13
(52) U.S. Cl. ................ 8/405; 8/405; 8/407; 8/408; 8/409; 8/410; 8/411; 8/416
(58) Field of Search ............. 8/405, 407, 408, 8/409, 410, 416, 411

(56) References Cited

U.S. PATENT DOCUMENTS

| | | | |
|---|---|---|---|
| 4,823,985 A | 4/1989 | Grollier et al. | 222/1 |
| 4,888,025 A | 12/1989 | Bugaut et al. | 8/405 |

FOREIGN PATENT DOCUMENTS

| | | |
|---|---|---|
| BE | 639 047 | 2/1964 |
| DE | 964 053 | 5/1957 |
| EP | 0 241 915 | 10/1987 |
| FR | 2 520 358 | 7/1983 |
| FR | 2 586 913 | 3/1997 |

OTHER PUBLICATIONS

Kimura et al. "Structure–activity relationship of N–(2–(Dimethylamino)–6–(3–(5–methyl–4–phenyl–H–imiidazol–1–yl)propoxy)phenyl)–N'–pentyllurea and analogoues." J.Med. Chem. 1993,36, 1630–1640.*
Chemical Abstracts, vol. 109, No. 5, Aug. 1, 1988, Abstract No. 34348.
Co–pending Application No. 09/646,454 (Int'l. Appln. No. PCT/FR99/00575), Inventors(s): Alain Genet et al., filed: Sep. 19, 2000.

* cited by examiner

*Primary Examiner*—Yogendra N. Gupta
*Assistant Examiner*—Eisa Elihilo
(74) *Attorney, Agent, or Firm*—Finnegan, Henderson, Farabow, Garrett & Dunner LLP

(57) ABSTRACT

The invention concerns an oxidation dyeing composition for keratinous fibers containing at least a monobenzene coupling agent including at least a cationic group Z bearing at least a cyclized or non-cyclized quaternary ammonium unit, the use of said coupling agents for dyeing keratinous fibers, dyeing methods using same, and novel monobenzene coupling agents comprising at least a cationic group Z bearing at least a cyclized or non-cylized quaternary ammonium.

62 Claims, No Drawings

OXIDATION DYEING COMPOSITIONS CONTAINING A CATIONIC COUPLING AGENT, NOVEL CATIONIC COUPLING AGENTS

The invention relates to a composition for the oxidation dyeing of keratin fibres, containing at least one monobenzenic coupler comprising at least one cationic group Z, Z being chosen from quaternized aliphatic chains and aliphatic chains containing at least one quaternized saturated ring, to the use of these couplers for dyeing keratin fibres, to oxidation dyeing processes using them and to novel monobenzenic couplers comprising at least one cationic group Z, Z being chosen from quaternized aliphatic chains and aliphatic chains containing at least one quaternized saturated ring.

It is known practice to dye keratin fibres, and in particular human hair, with dye compositions containing oxidation dye precursors, in particular ortho-phenylenediamines or para-phenylenediamines, ortho-aminophenols or para-aminophenols and heterocyclic compounds such as diaminopyrazole derivatives, which are generally referred to as oxidation bases. The oxidation dye precursors, or oxidation bases, are colourless or weakly coloured compounds which, when combined with oxidizing products, can give rise to coloured compounds and dyes by a process of oxidative condensation.

It is also known that the shades obtained with these oxidation bases can be varied by combining them with couplers or coloration modifiers, the latter being chosen in particular from aromatic meta-diamines, meta-aminophenols, meta-diphenols and certain heterocyclic compounds.

The variety of molecules used as oxidation bases and couplers makes it possible to obtain a wide range of colours.

The so-called "permanent" coloration obtained by means of these oxidation dyes must moreover satisfy a certain number of requirements. Thus, it must have no toxicological drawbacks and it must allow shades of the desired strength to be obtained and have good resistance to external agents (light, bad weather, washing, permanent-waving, perspiration and friction).

The dyes must also allow white hairs to be covered, and, lastly, they must be as unselective as possible, i.e. they must allow the smallest possible differences in coloration to be produced over the entire length of the same keratin fibre, which may indeed be differently sensitized (i.e. damaged) between its tip and its root.

It has already been proposed, in particular in patent application FR-A-2 520 358, to use certain cationic derivatives of meta-phenylenediamines, i.e. more specifically, certain meta-phenylenediamines monosubstituted with a quaternized aliphatic chain, for the oxidation dyeing of keratin fibres in intense shades. However, the use of the meta-phenylenediamines described in that prior patent application does not make it possible to obtain a wide variety of colours and, furthermore, the colorations obtained are not always entirely satisfactory as regards their resistance with respect to the various attacking factors to which the hair may be subjected (the action of light, perspiration, shampooing, etc.).

The Applicant has now discovered, entirely surprisingly and unexpectedly, that certain monobenzenic compounds of formula (I) defined below comprising at least one cationic group Z, Z being chosen from quaternized aliphatic chains and aliphatic chains containing at least one quaternized saturated ring, are not only suitable for use as couplers for oxidation dyeing, but also make it possible to obtain dye compositions which give intense colorations, in a very wide range of colours, and which have excellent properties of resistance to the various treatments to which the keratin fibres may be subjected. Finally, these compounds are found to be easy to synthesize.

These discoveries form the basis of the present invention.

A first subject of the invention is thus a composition for the oxidation dyeing of keratin fibres, and in particular of human keratin fibres such as the hair, characterized in that it comprises, in a medium which is suitable for dyeing, at least one monobenzenic coupler of formula (I) below, and/or at least one of the addition salts thereof with an acid:

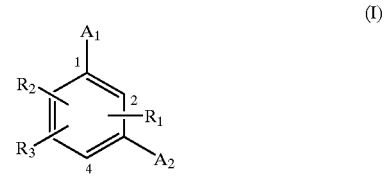

in which:

$R_1$, $R_2$ and $R_3$, which may be identical or different, represent a hydrogen atom; a halogen atom; a group Z; a group —CO—Z; a group —CO—OZ; a ($C_1$–$C_6$) alkylcarbonyl radical; an amino($C_1$–$C_6$)alkylcarbonyl radical; an N—Z-amino($C_1$–$C_6$)alkylcarbonyl radical; an N—($C_1$–$C_6$)alkylamino($C_1$–$C_6$)alkylcarbonyl radical; an N,N-di($C_1$–$C_6$)alkylamino($C_1$–$C_6$)alkylcarbonyl radical; an amino($C_1$–$C_6$)alkylcarbonyl($C_1$–$C_6$)alkyl radical; an N—Z-amino($C_1$–$C_6$)alkylcarbonyl($C_1$–$C_6$)alkyl radical; an N—($C_1$–$C_6$)alkylamino($C_1$–$C_6$)alkylcarbonyl($C_1$–$C_6$)alkyl radical; an N,N-di($C_1$–$C_6$)alkylamino($C_1$–$C_6$)alkylcarbonyl ($C_1$–$C_6$)alkyl radical; a carboxyl radical; a ($C_1$–$C_6$) alkylcarboxyl radical; a $C_1$–$C_6$ alkylsulphonyl radical; an aminosulphonyl radical; an N—Z-aminosulphonyl radical; a $C_1$–$C_6$ N-alkylaminosulphonyl radical; an N,N-di($C_1$–$C_6$) alkylaminosulphonyl radical; a $C_1$–$C_6$ aminosulphonylalkyl radical; a $C_1$–$C_6$ N—Z-aminosulphonylalkyl radical; an N—($C_1$–$C_6$)alkylaminosulphonyl($C_1$–$C_6$)alkyl radical; an N,N-di($C_1$–$C_6$)alkylaminosulphonyl($C_1$–$C_6$)alkyl radical; a carbamyl radical; an N—($C_1$–$C_6$)alkylcarbamyl radical; an N,N-di($C_1$–$C_6$)alkylcarbamyl radical; a carbamyl($C_1$–$C_6$) alkyl radical; an N—($C_1$–$C_6$)alkylcarbamyl ($C_1$–$C_6$)alkyl radical; an N,N-di ($C_1$–$C_6$)alkylcarbamyl ($C_1$–$C_6$)alkyl radical; a $C_1$–$C_6$ alkyl radical; a $C_1$–$C_6$ monohydroxyalkyl radical; a $C_2$–$C_6$ polyhydroxyalkyl radical; a ($C_1$–$C_6$)alkoxy ($C_1$–$C_6$)alkyl radical; a $C_1$–$C_6$ trifluoroalkyl radical; a cyano radical; a group $OR_6$ or $SR_6$; or an amino group protected with a ($C_1$–$C_6$)alkylcarbonyl, ($C_1$–$C_6$)alkylcarboxyl, trifluoro($C_1$–$C_6$)alkylcarbonyl, amino($C_1$–$C_6$) alkylcarbonyl, N—Z-amino($C_1$–$C_6$)alkylcarbonyl, N—($C_1$–$C_6$)alkylamino($C_1$–$C_6$)alkylcarbonyl, N,N-di ($C_1$–$C_6$)alkylamino($C_1$–$C_6$)alkylcarbonyl, ($C_1$–$C_6$) alkylcarboxyl, carbamyl, N—($C_1$–$C_6$)alkylcarbamyl, N,N-di($C_1$–$C_6$)alkylcarbamyl, $C_1$–$C_6$ alkylsulphonyl, aminosulphonyl, N—Z-aminosulphonyl, $C_1$–$C_6$ N-alkylaminosulphonyl, N,N-di($C_1$–$C_6$) alkylaminosulphonyl, thiocarbamyl or formyl radical, a group —CO—Z or a group —CO—OZ;

$R_6$ denotes a $C_1$–$C_6$ alkyl radical; a $C_1$–$C_6$ monohydroxyalkyl radical; a $C_2$–$C_6$ polyhydroxyalkyl radical; a group Z; a ($C_1$–$C_6$)alkoxy($C_1$–$C_6$)alkyl radical; an aryl radical; a benzyl radical; a carboxy($C_1$–$C_6$)alkyl radical; a ($C_1$–$C_6$)alkylcarboxy($C_1$–$C_6$)alkyl radical; a cyano($C_1$–$C_6$)alkyl radical; a carbamyl($C_1$–$C_6$)alkyl radical; an N—($C_1$–$C_6$)alkylcarbamyl($C_1$–$C_6$)alkyl radical; an N,N-di ($C_1$–$C_6$)alkylcarbamyl($C_1$–$C_6$)alkyl radical; a $C_1$–$C_6$ trifluoroalkyl radical; a $C_1$–$C_6$ aminosulphonylalkyl radical; a $C_1$–$C_6$ N—Z-aminosulphonylalkyl radical; an N—($C_1$–$C_6$) alkylaminosulphonyl($C_1$–$C_6$)alkyl radical; an N,N-di ($C_1$–$C_6$)alkylaminosulphonyl($C_1$–$C_6$)alkyl radical; a ($C_1$–$C_6$)alkylsulphinyl($C_1$–$C_6$)alkyl radical; a ($C_1$–$C_6$) alkylsulphonyl($C_1$–$C_6$)alkyl radical; a ($C_1$–$C_6$) alkylcarbonyl($C_1$–$C_6$)alkyl radical; a $C_1$–$C_6$ aminoalkyl radical; a $C_1$–$C_6$ aminoalkyl radical in which the amine is substituted with one or two identical or different radicals chosen from $C_1$–$C_6$ alkyl, $C_1$–$C_6$ monohydroxyalkyl, $C_2$–$C_6$ polyhydroxyalkyl, ($C_1$–$C_6$) alkylcarbonyl, formyl, trifluoro-($C_1$–$C_6$)alkylcarbonyl, ($C_1$–$C_6$)alkylcarboxyl, carbamyl, N—($C_1$–$C_6$) alkylcarbamyl, N,N-di-($C_1$–$C_6$)alkylcarbamyl, thiocarbamyl and $C_1$–$C_6$ alkylsulphonyl radicals, and from the groups Z, —CO—Z and —CO—OZ;

A1 represents a group —$NR_4R_5$ or a hydroxyl radical;

A2 represents a group —$NR'_4R'_5$ or a hydroxyl radical;

$R_4$, $R'_4$, $R_5$ and $R'_5$, which may be identical or different, represent a hydrogen atom; a group Z; a $C_1$–$C_6$ alkyl radical; a $C_1$–$C_6$ monohydroxyalkyl radical; a $C_2$–$C_6$ polyhydroxyalkyl radical; a ($C_1$–$C_6$)alkoxy($C_1$–$C_6$) alkyl radical; an aryl radical; a benzyl radical; a cyano ($C_1$–$C_6$)alkyl radical; a carbamyl($C_1$–$C_6$)alkyl radical; an N—($C_1$–$C_6$)alkylcarbamyl($C_1$–$C_6$)alkyl radical; an N,N-di($C_1$–$C_6$)alkylcarbamyl($C_1$–$C_6$)alkyl radical; a thiocarbamyl($C_1$–$C_6$)alkyl radical; a $C_1$–$C_6$ trifluoroalkyl radical; a $C_1$–$C_6$ sulphoalkyl radical; a ($C_1$–$C_6$) alkylcarboxy($C_1$–$C_6$)alkyl radical; a ($C_1$–$C_6$) alkylsulphinyl($C_1$–$C_6$)alkyl radical; a $C_1$–$C_6$ aminosulphonylalkyl radical; a $C_1$–$C_6$ N—Z-aminosulphonylalkyl radical; an N—($C_1$–$C_6$) alkylaminosulphonyl($C_1$–$C_6$)alkyl radical; an N,N-di ($C_1$–$C_6$)alkylaminosulphonyl($C_1$–$C_6$)alkyl radical; a ($C_1$–$C_6$)alkylcarbonyl($C_1$–$C_6$)alkyl radical; a $C_1$–$C_6$ aminoalkyl radical; a $C_1$–$C_6$ aminoalkyl radical in which the amine is substituted with one or two identical or different radicals chosen from $C_1$–$C_6$ alkyl, $C_1$–$C_6$ monohydroxyalkyl, $C_2$–$C_6$ polyhydroxyalkyl, ($C_1$–$C_6$) alkylcarbonyl, carbamyl, N—($C_1$–$C_6$)alkylcarbamyl or N,N-di($C_1$–$C_6$)alkylcarbamyl, $C_1$–$C_6$ alkylsulphonyl, formyl, trifluoro($C_1$–$C_6$)alkylcarbonyl, ($C_1$–$C_6$) alkylcarboxyl and thiocarbamyl radicals, or with a group Z, —CO—Z or —CO—OZ;

one and only one of the radicals $R_4$, $R'_4$, $R_5$ and $R'_5$ can also represent a ($C_1$–$C_6$)alkylcarboxyl radical; a ($C_1$–$C_6$)alkylcarbonyl radical; a formyl radical; a trifluoro($C_1$–$C_6$)alkylcarbonyl radical; an amino ($C_1$–$C_6$)alkylcarbonyl radical; an N-Z-amino ($C_1$–$C_6$)alkylcarbonyl radical; an N—($C_1$–$C_6$) alkylamino($C_1$–$C_6$)alkylcarbonyl radical; an N,N-di ($C_1$–$C_6$)alkylamino($C_1$–$C_6$)alkylcarbonyl radical; a carbamyl radical; an N—($C_1$–$C_6$)alkylcarbamyl radical; an N,N-di($C_1$–$C_6$)alkylcarbamyl radical; a thiocarbamyl radical; an aminosulphonyl radical; an N—Z-aminosulphonyl radical; an N—($C_1$–$C_6$) alkylaminosulphonyl radical; an N,N-di($C_1$–$C_6$) alkylaminosulphonyl radical; a ($C_1$–$C_6$) alkylsulphonyl radical; a group —CO—Z or a group —CO—OZ;

Z represents a group of formula (II) below:

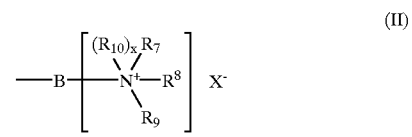

in which:

B is a linker arm which represents a linear or branched alkyl chain preferably containing from 1 to 14 carbon atoms, which may be interrupted by one or more hetero atoms such as oxygen, sulphur or nitrogen atoms, and which may be substituted with one or more hydroxyl or $C_1$–$C_6$ alkoxy radicals;

$R_7$, $R_8$ and $R_9$, which may be identical or different, represent a $C_1$–$C_6$ alkyl radical; a $C_1$–$C_6$ monohydroxyalkyl radical; a $C_2$–$C_6$ polyhydroxyalkyl radical; a ($C_1$–$C_6$)alkoxy($C_1$–$C_6$)alkyl radical; a cyano ($C_1$–$C_6$)alkyl radical; an aryl radical; a benzyl radical; a carbamyl($C_1$–$C_6$)alkyl radical; a tri ($C_1$–$C_6$)alkylsilane($C_1$–$C_6$)alkyl radical or a $C_1$–$C_6$ aminoalkyl radical in which the amine is protected with a ($C_1$–$C_6$)alkylcarbonyl, carbamyl or ($C_1$–$C_6$) alkylsulphonyl radical; two of the radicals $R_7$, $R_8$ and $R_9$ can also form, together with the nitrogen atom to which they are attached, a 5- or 6-membered saturated carbon-based ring or a ring containing one or more hetero atoms such as, for example, a pyrrolidone ring, a piperidine ring, a piperazine ring or a morphotine ring, it being possible for the said ring to be unsubstituted or substituted with a halogen atom, a hydroxyl radical, a $C_1$–$C_6$ alkyl radical, a $C_1$–$C_6$ monohydroxyalkyl radical, a $C_2$–$C_6$ polyhydroxyalkyl radical, a nitro radical, a cyano radical, a cyano($C_1$–$C_6$)alkyl radical, a $C_1$–$C_6$ alkoxy radical, a tri($C_1$–$C_6$)alkylsilane($C_1$–$C_6$)alkyl radical, an amido radical, an aldehydo radical, a carboxyl radical, a ($C_1$–$C_6$)alkylcarbonyl radical, a thio radical, a $C_1$–$C_6$ thioalkyl radical, a ($C_1$–$C_6$) alkylthio radical, an amino radical, an amino radical protected with a ($C_1$–$C_6$)alkylcarbonyl, carbamyl or ($C_1$–$C_6$)alkylsulphonyl radical; one of the radicals $R_7$, $R_8$ and $R_9$ can also represent a linker arm B' of a second radical Z, B' having the same meaning as that given above for the radical B;

$X^-$ represents a monovalent or divalent anion and is preferably chosen from a halogen atom such as chlorine, bromine, fluorine or iodine, a hydroxide, a hydrogen sulphate or a $C_1$–$C_6$ alkyl sulphate such as, for example, a methyl sulphate or an ethyl sulphate;

$R_{10}$ represents a $C_1$–$C_6$ alkyl radical; a $C_1$–$C_6$ monohydroxyalkyl radical; a $C_2$–$C_6$ polyhydroxyalkyl radical; an aryl radical; a benzyl radical; a $C_1$–$C_6$ aminoalkyl radical, a $C_1$–$C_6$ aminoalkyl radical in which the amine is protected with a ($C_1$–$C_6$) alkylcarbonyl, carbamyl or $C_1$–$C_6$ alkylsulphonyl radical; a carboxy($C_1$–$C_6$)alkyl radical; a cyano ($C_1$–$C_6$)alkyl radical; a carbamyl($C_1$–$C_6$)alkyl radical; a $C_1$–$C_6$ trifluoroalkyl radical; a tri($C_1$–$C_6$) alkylsilane($C_1$–$C_6$)alkyl radical; a $C_1$–$C_6$ sulphonamidoalkyl radical; a ($C_1$–$C_6$)alkylcarboxy ($C_1$–$C_6$)alkyl radical; a ($C_1$–$C_6$)alkylsulphinyl ($C_1$–$C_6$)alkyl radical; a ($C_1$–$C_6$)alkylsulphonyl ($C_1$–$C_6$)alkyl radical; a ($C_1$–$C_6$)alkylketo($C_1$–$C_6$) alkyl radical; an N—($C_1$–$C_6$)alkylcarbamyl($C_1$–$C_6$) alkyl radical; an N—($C_1$–$C_6$)alkylsulphonamido ($C_1$–$C_6$)alkyl radical;

x is an integer equal to 0 or 1; with the following conditions:
   when x=0, then the linker arm B is attached to the nitrogen atom bearing the radicals $R_7$ to $R_9$;
   when x=1, then two of the radicals $R_7$ to $R_9$ form, together with the nitrogen atom to which they are attached, a saturated 5- or 6-membered ring as defined above, and the linker arm B is borne by a carbon atom of the said saturated ring;
it being understood that:
   the number of groups Z is at least equal to 1;
   when the compounds of formula (I) comprise only one group Z, and when A1 and A2 respectively denote—$NR_4R_5$ and —$NR'_4R'_5$ in which:
      either the radicals $R_4$ and $R_5$, which may be identical or different, represent a hydrogen atom or a $C_1$–$C_6$ alkyl or $C_1$–$C_6$ hydroxyalkyl radical, and the radicals $R'_4$ and $R'_5$ simultaneously represent a hydrogen atom,
      or $R_4$ and $R_5$ simultaneously represent a hydrogen atom and the radicals $R'_4$ and $R'_5$, which may be identical or different, represent a hydrogen atom or a $C_1$–$C_6$ alkyl or $C_1$–$C_6$ hydroxyalkyl radical,
and when only one of the radicals $R_1$ to $R_3$ represents a group $OR_6$ in which $R_6$ represents a group Z in which the linker arm B is a $C_3$ alkyl chain monosubstituted in position 2 with a hydroxyl radical and in which the radicals $R_7$, $R_8$ and $R_9$, which may be identical or different, represent a $C_1$–$C_6$ alkyl or $C_1$–$C_6$ hydroxyalkyl radical or together form, with the nitrogen atom to which they are attached, a morpholine or piperidine ring, then the other two radicals $R_1$ to $R_3$ cannot simultaneously denote a hydrogen atom.

As mentioned above, the colorations obtained with the oxidation dye composition in accordance with the invention are strong and produce a wide range of shades and colours. They moreover have excellent properties of resistance to the action of various external agents (light, bad weather, washing, permanent-waving, perspiration, friction).

In formula (I) above, the alkyl and alkoxy radicals can be linear or branched.

Among the compounds of formula (I) above which may be mentioned in particular, are:

[2-(2,4-diaminophenoxy)ethyl]diethylmethylammonium chloride
1-[3-(2,4-diaminophenoxy)propyl]-1,4-dimethylpiperazin-1-ium chloride;
1-[(3-hydroxy-4-methylphenylcarbamoyl)methyl]-1,4-dimethylpiperazin-1-ium chloride;
1,4-bis(2-hydroxyethyl)-1-[(3-hydroxyphenylcarbamoyl)methyl]piperazin-1-ium chloride;
[3-(2,4-diaminophenoxy)propyl]triethylammonium chloride;
1-[(2,4-dihydroxyphenylcarbamoyl)methyl]-1-methylpiperidinium chloride;
[2-(2,4-dihydroxyphenyl)-2-oxoethyl]triethylammonium chloride;
1-[(3-hydroxy-4-methylphenylcarbamoyl)methyl]-1-methylpyrrolidinium chloride;
1-[(2,6-dihydroxyphenylcarbamoyl)methyl]-1-methylpyrrolidinium chloride;
[2-(4-amino-2-hydroxyphenoxy)ethyl]diethylmethylammonium chloride;
triethyl-[2-(3-hydroxy-4-methylphenylamino)ethyl]ammonium bromide;
1-[2-(3-hydroxy-4-methylphenylamino)ethyl]-1,4-dimethylpiperazin-1-ium bromide;
4-[(3-hydroxyphenylcarbamoyl)methyl]-4-methylmorpholin-4-ium chloride;
triethyl-[2-(3-hydroxy-2,4-dimethylphenylcarbamoyloxy)ethyl]ammonium chloride;
[2-(4-chloro-3-hydroxyphenylamino)ethyl]triethylammonium bromide;
1-[3-(2-amino-4-methylaminophenoxy)propyl]-1-methylpiperidinium chloride;
[2-(2,4-diaminophenoxy)ethyl]diethylmethylammonium chloride;
1-(3-trimethylammonium-2-hydroxypropyl)-1-[(3-hydroxy-4-methylphenylcarbamoyl)methyl]pyrrolidinium dichloride;
1-[2-(3-amino-4-methoxyphenylamino)ethyl]-1,4-dimethylpiperazin-1-ium bromide;
[2-(2,4-diaminophenyl)ethyl]triethylammonium chloride;
1-[(3-hydroxy-2,4-dimethylphenylcarbamoyl)methyl]-1,4-dimethylpiperazin-1-ium chloride;
N,N-bis[2-(1-methylpyrrolidinium)ethyl]benzene-1,3-diamine dichloride;
triethyl[(3-hydroxy-4-methylphenylcarbamoyl)methyl]ammonium chloride;
N,N'-bis{2-[1,4-bis(2-hydroxyethyl)piperazin-1-ium]ethyl}benzene-1,3-diamine-2-methyl dichloride;
1-[3-(2,4-diaminophenoxy)propyl]-1-methylpyrrolidinium chloride;
1-[(3-hydroxyphenylcarbamoyl)methyl]-1,4-dimethylpiperazin-1-ium chloride;
1-[3-(2,4-diaminophenoxy)propyl]-4-(3-trimethylammonium-2-hydroxypropyl)-1,4-dimethylpiperazine-1,4-diium trichloride;
[2-[4-(dimethylamino)salicylamido]ethyl]diethylmethylammonium iodide;
ethyl(2-hydroxyethyl)dimethylammonium 4-(methylamino)salicylate bromide;
3-[(4-amino-2-hydroxybenzoyl)oxy]-N-ethyl-N,N-dimethyl-1-propanaminium iodide;
3-[(4-amino-2-hydroxybenzoyl)oxy]-N,N,N-trimethyl-1-propanaminium iodide;
triethyl(2-hydroxyethyl)ammonium 4-aminosalicylate bromide;
2-[(4-amino-2-hydroxybenzoyl)oxy]-N,N-diethyl-N-methylethanaminium iodide;
2-[(4-amino-2-hydroxybenzoyl)oxy]-N-ethyl-N,N-dimethylethanaminium iodide;
ethyl(2-hydroxyethyl)dimethylammonium 4-aminosalicylate bromide;
2-[(4-amino-2-hydroxybenzoyl)oxy]-N,N,N-trimethylethanaminium iodide;

and the addition salts thereof with an acid.

Among these compounds of formula (I), the ones more particularly preferred are:

[2-(2,4-diaminophenoxy)ethyl]diethylmethylammonium chloride;
1-[3-(2,4-diaminophenoxy)propyl]-1,4-dimethylpiperazin-1-ium chloride;
1-[(3-hydroxy-4-methylphenylcarbamoyl)methyl]-1,4-dimethylpiperazin-1-ium chloride;
1,4-bis(2-hydroxyethyl)-1-[(3-hydroxyphenylcarbamoyl)methyl]piperazin-1-ium chloride;
[3-(2,4-diaminophenoxy)propyl]triethylammonium chloride;
1-[(2,4-dihydroxyphenylcarbamoyl)methyl]-1-methylpiperidinium chloride;
[2-(2,4-dihydroxyphenyl)-2-oxoethyl]triethylammonium chloride;
1-[(3-hydroxy-4-methylphenylcarbamoyl)methyl]-1-methylpyrrolidinium chloride;

1-[(2,6-dihydroxyphenylcarbamoyl)methyl]-1-methylpyrrolidinium chloride;
[2-(4-amino-2-hydroxyphenoxy)ethyl]diethylmethylammonium chloride;
triethyl[2-(3-hydroxy-4-methylphenylamino)ethyl]ammonium bromide;
1-[2-(3-hydroxy-4-methylphenylamino)ethyl]-1,4-dimethylpiperazin-1-ium bromide;
4-[(3-hydroxyphenylcarbamoyl)methyl]-4-methylmorpholin-4-ium chloride;
triethyl[2-(3-hydroxy-2,4-dimethylphenylcarbamoyloxy)ethyl]ammonium chloride;
[2-(4-chloro-3-hydroxyphenylamino)ethyl]triethylammonium bromide;
1-[3-(2-amino-4-methylaminophenoxy)propyl]-1-methylpiperidinium chloride;
[2-(2,4-diaminophenoxy)ethyl]diethylmethylammonium chloride;
1-(3-trimethylammonium-2-hydroxypropyl)-1-[(3-hydroxy-4-methylphenylcarbamoyl)methyl]pyrrolidinium dichloride;
1-[2-(3-amino-4-methoxyphenylamino)ethyl]-1,4-dimethylpiperazin-1-ium bromide;
[2-(2,4-diaminophenyl)ethyl]triethylammonium chloride;
1-[(3-hydroxy-2,4-dimethylphenylcarbamoyl)methyl]-1,4-dimethylpiperazin-1-ium chloride;
N,N-bis[2-(1-methylpyrrolidinium)ethyl]benzene-1,3-diamine dichloride;
triethyl[(3-hydroxy-4-methylphenylcarbamoyl)methyl]ammonium chloride;
N,N'-bis{2-[1,4-bis(2-hydroxyethyl)piperazin-1-ium]ethyl}benzene-1,3-diamine-2-methyl dichloride;
1-[3-(2,4-diaminophenoxy)propyl]-1-methylpyrrolidinium chloride;
1-[(3-hydroxyphenylcarbamoyl)methyl]-1,4-dimethylpiperazin-1-ium chloride;
1-[3-(2,4-diaminophenoxy)propyl]-4-(3-trimethylammonium-2-hydroxypropyl)-1,4-dimethylpiperazine-1,4-diium trichloride;

and the addition salts thereof with an acid.

The compound(s) of formula (I) in accordance with the invention and/or the addition salt(s) thereof with an acid preferably represent(s) from 0.0005 to 12% by weight approximately relative to the total weight of the dye composition, and even more preferably from 0.005 to 6% by weight approximately relative to this weight.

According to one preferred embodiment of the invention, the dye composition also includes one or more oxidation bases which can be chosen from the oxidation bases conventionally used in oxidation dyeing and among which mention may be made in particular of para-phenylenediamines, bis(phenyl)alkylenediamines, para-aminophenols, ortho-aminophenols and heterocyclic bases.

Among the para-phenylenediamines which can be mentioned more particularly, for example, are para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N-ethyl-N-(β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine and N-(β-methoxyethyl)-para-phenylenediamine, and the addition salts thereof with an acid.

Among the para-phenylenediamines mentioned above, the ones most particularly preferred are para-phenylenediamine, para-tolylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine and 2-β-acetylaminoethyloxy-para-phenylenediamine, and the addition salts thereof with an acid.

Among the bis(phenyl)alkylenediamines which can be mentioned more particularly, for example, are N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetra-methylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl)ethylenediamine and 1,8-bis(2,5-diaminophenoxy)-3,5-dioxaoctane, and the addition salts thereof with an acid.

Among the para-aminophenols which can be mentioned more particularly, for example, are para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol and 4-amino-2-fluorophenol, and the addition salts thereof with an acid.

Among the ortho-aminophenols which can be mentioned more particularly, for example, are 2-aminophenol, 2-amino-5-methylphenol, 2-amino-6-methylphenol and 5-acetamido-2-aminophenol, and the addition salts thereof with an acid.

Among the heterocyclic bases which can be mentioned more particularly, for example, are pyridine derivatives, pyrimidine derivatives and pyrazole derivatives.

When they are used, the oxidation base(s) preferably represent(s) from 0.0005 to 12% by weight approximately relative to the total weight of the dye composition, and even more preferably from 0.005 to 6% by weight approximately relative to this weight.

In addition to the compound(s) of formula (I) above, the dye composition in accordance with the invention can also include one or more additional couplers which can be chosen from the couplers used conventionally in oxidation dyeing and among which mention may be made in particular of meta-phenylenediamines other than the meta-phenylenediamines of formula (I), meta-aminophenols other than the meta-aminophenols of formula (I), meta-diphenols and heterocyclic couplers such as, for example, indole derivatives, indolene derivatives, pyridine derivatives and pyrazolones, and the addition salts thereof with an acid.

These couplers are chosen more particularly from 2-methyl-5-aminophenol, 5-N-(β-hydroxyethyl)amino-2- methylpenol, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, sesamol, α-naphthol, 6-hydroxyindole, 4-hydroxyindole, 4-hydroxy-N-methylindole, 6-hydroxyindoline, 2,6-dihydroxy-4-methylpyridine, 1H-3-methylpyrazol-5-one and 1-phenyl-3-methylpyrazol-5-one, and the addition salts thereof with an acid.

When they are present, the coupler(s) preferably represent(s) from 0.0001 to 10% by weight approximately relative to the total weight of the dye composition and even more preferably from 0.005 to 5% by weight approximately relative to this weight.

In general, the addition salts with an acid which can be used in the context of the dye compositions of the invention (compounds of formula (I), additional oxidation bases and couplers) are chosen in particular from the hydrochlorides, hydrobromides, sulphates, citrates, succinates, tartrates, lactates and acetates.

The medium which is suitable for dyeing (or support) generally consists of water or a mixture of water and at least one organic solvent to dissolve the compounds which would not be sufficiently soluble in water. As organic solvent, mention may be made, for example, of $C_1$–$C_4$ lower alkanols, such as ethanol and isopropanol; glycerol; glycols and glycol ethers such as 2-butoxyethanol, propylene glycol, propylene glycol monomethyl ether, diethylene glycol monoethyl ether and monomethyl ether, as well as aromatic alcohols such as benzyl alcohol or phenoxyethanol, similar products and mixtures thereof.

The solvents can be present in proportions preferably of between 1 and 40% by weight approximately relative to the total weight of the dye composition, and even more preferably between 5 and 30% by weight approximately.

The pH of the dye composition in accordance with the invention is generally between 3 and 12 approximately, and preferably between 5 and 11 approximately. It can be adjusted to the desired value using acidifying or basifying agents commonly used to dye keratin fibres.

Among the acidifying agents which may be mentioned, for example, are inorganic or organic acids such as hydrochloric acid, orthophosphoric acid, sulphuric acid, carboxylic acids such as acetic acid, tartaric acid, citric acid and lactic acid, and sulphonic acids.

Among the basifying agents which can be mentioned, for example, are aqueous ammonia, alkaline carbonates, alkanolamines such as mono-, di- and triethanolamine and derivatives thereof, sodium hydroxide, potassium hydroxide and the compounds of formula (III) below:

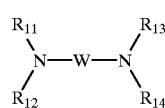

(III)

in which W is a propylene residue optionally substituted with a hydroxyl group or a $C_1$–$C_6$ alkyl radical; $R_{11}$, $R_{12}$, $R_{13}$ and $R_{14}$, which may be identical or different, represent a hydrogen atom, a $C_1$–$C_6$ alkyl radical or a $C_1$–$C_6$ hydroxyalkyl radical.

The oxidation dye compositions in accordance with the invention can also include at least one direct dye, in particular in order to modify the shades or to enrich them with glints.

The dye composition in accordance with the invention can also contain various adjuvants conventionally used in compositions for dyeing the hair, such as anionic, cationic, nonionic, amphoteric or zwitterionic surfactants or mixtures thereof, anionic, cationic, nonionic, amphoteric or zwitterionic polymers or mixtures thereof, inorganic or organic thickeners, antioxidants, penetration agents, sequestering agents, fragrances, buffers, dispersing agents, packaging agents such as, for example, silicones, which may or may not be volatile or modified, film-forming agents, ceramides, preserving agents and opacifiers.

Needless to say, a person skilled in the art will take care to select this or these optional additional compound(s) such that the advantageous properties intrinsically associated with the oxidation dye composition in accordance with the invention are not, or are not substantially, adversely affected by the addition(s) envisaged.

The dye composition according to the invention can be in various forms, such as in the form of liquids, creams or gels or in any other form which is suitable for dyeing keratin fibres, and in particular human hair.

The invention also relates to a process for the oxidation dyeing of keratin fibres, and in particular of human keratin fibres such as the hair, using the dye composition as defined above.

According to this process, at least one dye composition as defined above is applied to the fibres, the colour being developed at acidic, neutral or alkaline pH using an oxidizing agent which is added, just at the time of use, to the dye composition, or which is present in an oxidizing composition that is applied simultaneously or sequentially.

According to a preferred embodiment of the dyeing process of the invention, the dye composition described above is preferably mixed, at the time of use, with an oxidizing composition containing, in a medium which is suitable for dyeing, at least one oxidizing agent present in an amount which is sufficient to develop a coloration. The mixture obtained is then applied to the keratin fibres and is left in place for 3 to 50 minutes approximately, preferably 5 to 30 minutes approximately, after which the fibres are rinsed, washed with shampoo, rinsed again and dried.

The oxidizing agent can be chosen from the oxidizing agents conventionally used for the oxidation dyeing of keratin fibres, and among which mention may be made of hydrogen peroxide, urea peroxide, alkali metal bromates, persalts such as perborates and persulphates, and enzymes such as peroxidases and 2-electron oxidoreductases. Hydrogen peroxide is particularly preferred.

The pH of the oxidizing composition containing the oxidizing agent as defined above is such that, after mixing with the dye composition, the pH of the resultant composition applied to the keratin fibres preferably varies between 3 and 12 approximately, and even more preferably between 5 and 11. It is adjusted to the desired value using acidifying or basifying agents commonly used to dye keratin fibres and as defined above.

The oxidizing composition as defined above can also contain various adjuvants conventionally used in compositions for dyeing the hair and as defined above.

The composition which is finally applied to the keratin fibres can be in various forms, such as in the form of liquids, creams, gels or any other form which is suitable for dyeing keratin fibres, and in particular human hair.

Another subject of the invention is a multi-compartment dyeing device or "kit" or any other multi-compartment packaging system, a first compartment of which contains the dye composition as defined above and a second compartment of which contains the oxidizing composition as defined above. These devices can be equipped with a means for delivering the desired mixture onto the hair, such as the devices described in patent FR 2 586 913 in the name of the Applicant.

Certain compounds of formula (I) are novel per se and in this respect constitute another subject of the invention. These novel compounds, as well as the addition salts thereof with an acid, correspond to formula (I') below:

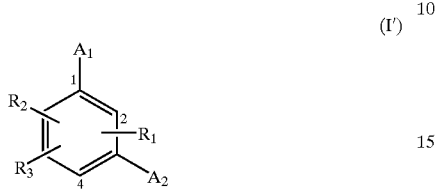

(I')

in which $R_1$, $R_2$ and $R_3$, which may be identical or different, represent a hydrogen atom; a halogen atom; a group Z; a group —CO—Z; a group —CO—OZ; a ($C_1$–$C_6$) alkylcarbonyl radical; an amino($C_1$–$C_6$)alkylcarbonyl radical; an N—Z-amino ($C_1$–$C_6$)alkylcarbonyl radical; an N—($C_1$–$C_6$)alkylamino($C_1$–$C_6$)alkylcarbonyl radical; an N,N-di($C_1$–$C_6$)alkylamino($C_1$–$C_6$) alkylcarbonyl radical; an amino($C_1$–$C_6$)alkylcarbonyl ($C_1$–$C_6$)alkyl radical; an N—Z-amino($C_1$–$C_6$) alkylcarbonyl($C_1$–$C_6$)alkyl radical; an N—($C_1$–$C_6$) alkylamino($C_1$–$C_6$)alkylcarbonyl($C_1$–$C_6$)alkyl radical; an N,N-di($C_1$–$C_6$)alkylamino($C_1$–$C_6$)alkyl-carbonyl ($C_1$–$C_6$)alkyl radical; a carboxyl radical; a ($C_1$–$C_6$) alkylcarboxyl radical; a $C_1$–$C_6$ alkylsulphonyl radical; an aminosulphonyl radical; an N-Z-aminosulphonyl radical; a $C_1$–$C_6$ N-alkylaminosulphonyl radical; an N,N-di($C_1$–$C_6$)alkylaminosulphonyl radical; a $C_1$–$C_6$ aminosulphonylalkyl radical; a $C_1$–$C_6$ N—Z-aminosulphonylalkyl radical; an N—($C_1$–$C_6$) alkylaminosulphonyl($C_1$–$C_6$)alkyl radical; an N,N-di ($C_1$–$C_6$)alkylaminosulphonyl($C_1$–$C_6$)alkyl radical; a carbamyl radical; an N—($C_1$–$C_6$)alkylcarbamyl radical; an N,N-di($C_1$–$C_6$)alkylcarbamyl radical; a carbamyl($C_1$–$C_6$)alkyl radical; an N—($C_1$–$C_6$)alkyl-carbamyl($C_1$–$C_6$)alkyl radical; an N,N-di($C_1$–$C_6$)alkyl-carbamyl($C_1$–$C_6$)alkyl radical; a $C_1$–$C_6$ alkyl radical; a $C_1$–$C_6$ monohydroxyalkyl radical; a $C_2$–$C_6$ polyhydroxy-alkyl radical; a ($C_1$–$C_6$)alkoxy($C_1$–$C_6$) alkyl radical; a $C_1$–$C_6$ trifluoroalkyl radical; a cyano radical; a group $OR_6$ or $SR_6$; or an amino group protected with a ($C_1$–$C_6$)alkylcarbonyl, ($C_1$–$C_6$) alkylcarboxyl, trifluoro($C_1$–$C_6$)alkylcarbonyl, amino ($C_1$–$C_6$)alkyl-carbonyl, N—Z-amino ($C_1$–$C_6$) alkylcarbonyl, N—($C_1$–$C_6$)alkylamino($C_1$–$C_6$) alkylcarbonyl, N,N-di($C_1$–$C_6$)alkylamino($C_1$–$C_6$) alkylcarbonyl, ($C_1$–$C_6$)alkylcarboxyl, carbamyl, N—($C_1$–$C_6$)alkyl-carbamyl, N,N-di($C_1$–$C_6$) alkylcarbamyl, $C_1$–$C_6$ alkylsulphonyl, aminosulphonyl, N—Z-aminosulphonyl, $C_1$–$C_6$ N-alkylaminosulphonyl, N,N-di($C_1$–$C_6$)alkylamino-sulphonyl, thiocarbamyl or formyl radical, a group —CO—Z or a group —CO—OZ;

$R_6$ denotes a $C_1$–$C_6$ alkyl radical; a $C_1$–$C_6$ monohydroxy-alkyl radical; a $C_2$–$C_6$ polyhydroxyalkyl radical; a group Z; a ($C_1$–$C_6$)alkoxy($C_1$–$C_6$)alkyl radical; an aryl radical; a benzyl radical; a carboxy($C_1$–$C_6$)alkyl radical; a ($C_1$–$C_6$)alkylcarboxy-($C_1$–$C_6$)alkyl radical; a cyano($C_1$–$C_6$)alkyl radical; a carbamyl($C_1$–$C_6$)alkyl radical; an N—($C_1$–$C_6$)alkyl-carbamyl($C_1$–$C_6$)alkyl radical; an N,N-di($C_1$–$C_6$)alkyl-carbamyl($C_1$–$C_6$)alkyl radical; a $C_1$–$C_6$ trifluoroalkyl radical; a $C_1$–$C_6$ aminosulphonylalkyl radical; a $C_1$–$C_6$ N—Z-aminosulphonylalkyl radical; an N—($C_1$–$C_6$) alkylaminosulphonyl($C_1$–$C_6$)alkyl radical; an N,N-di ($C_1$–$C_6$)alkylaminosulphonyl($C_1$–$C_6$)alkyl radical; a ($C_1$–$C_6$)alkylsulphinyl($C_1$–$C_6$)alkyl radical; a ($C_1$–$C_6$) alkylsulphonyl($C_1$–$C_6$)alkyl radical; a ($C_1$–$C_6$) alkylcarbonyl($C_1$–$C_6$)alkyl radical; a $C_1$–$C_6$ aminoalkyl radical; a $C_1$–$C_6$ aminoalkyl radical in which the amine is substituted with one or two identical or different radicals chosen from $C_1$–$C_6$ alkyl, $C_1$–$C_6$ monohydroxyalkyl, $C_2$–$C_6$ polyhydroxyalkyl, ($C_1$–$C_6$) alkylcarbonyl, formyl, trifluoro-($C_1$–$C_6$)alkylcarbonyl, ($C_1$–$C_6$)alkylcarboxyl, carbamyl, N—($C_1$–$C_6$) alkylcarbamyl, N,N-di-($C_1$–$C_6$)alkylcarbamyl, thiocarbamyl and $C_1$–$C_6$ alkylsulphonyl radicals, and from the groups Z, —CO—Z and —CO—OZ;

A1 represents a group —$NR_4R_5$ or a hydroxyl radical;

A2 represents a group —$NR'_4R'_5$ or a hydroxyl radical;

$R_4$, $R'_4$, $R_5$ and $R'_5$, which may be identical or different, represent a hydrogen atom; a group Z; a $C_1$–$C_6$ alkyl radical; a $C_1$–$C_6$ monohydroxyalkyl radical; a $C_2$–$C_6$ polyhydroxyalkyl radical; a ($C_1$–$C_6$)alkoxy($C_1$–$C_6$) alkyl radical; an aryl radical; a benzyl radical; a cyano ($C_1$–$C_6$)alkyl radical; a carbamyl($C_1$–$C_6$)alkyl radical; an N—($C_1$–$C_6$)alkylcarbamyl ($C_1$–$C_6$)alkyl radical; an N,N-di($C_1$–$C_6$)alkylcarbamyl($C_1$–$C_6$)alkyl radical; a thiocarbamyl($C_1$–$C_6$)alkyl radical; a $C_1$–$C_6$ trifluoro-alkyl radical; a $C_1$–$C_6$ sulphoalkyl radical; a ($C_1$–$C_6$) alkylcarboxy($C_1$–$C_6$)alkyl radical; a ($C_1$–$C_6$) alkylsulphinyl($C_1$–$C_6$)alkyl radical; a $C_1$–$C_6$ aminosulphonylalkyl radical; a $C_1$–$C_6$ N—Z-aminosulphonylalkyl radical; an N—($C_1$–$C_6$) alkylaminosulphonyl($C_1$–$C_6$)alkyl radical; an N,N-di ($C_1$–$C_6$)alkylaminosulphonyl($C_1$–$C_6$)alkyl radical; a ($C_1$–$C_6$)alkylcarbonyl($C_1$–$C_6$)alkyl radical; a $C_1$–$C_6$ aminoalkyl radical; a $C_1$–$C_6$ aminoalkyl radical in which the amine is substituted with one or two identical or different radicals chosen from $C_1$–$C_6$ alkyl, $C_1$–$C_6$ monohydroxyalkyl, $C_2$–$C_6$ polyhydroxyalkyl, ($C_1$–$C_6$) alkylcarbonyl, carbamyl, N—($C_1$–$C_6$)alkylcarbamyl or N,N-di($C_1$–$C_6$)alkylcarbamyl, $C_1$–$C_6$ alkylsulphonyl, formyl, trifluoro($C_1$–$C_6$)alkylcarbonyl, ($C_1$–$C_6$) alkylcarboxyl and thiocarbamyl radicals, or with a group Z, —CO—Z or —CO—OZ; one and only one of the radicals $R_4$, $R'_4$, $R_5$ and $R'_5$ can also represent a ($C_1$–$C_6$)alkylcarboxyl radical; a ($C_1$–$C_6$)alkylcarbonyl radical; a formyl radical; a trifluoro($C_1$–$C_6$) alkylcarbonyl radical; an amino($C_1$–$C_6$)alkylcarbonyl radical; an N—Z-amino($C_1$–$C_6$)alkylcarbonyl radical; an N—($C_1$–$C_6$)alkylamino($C_1$–$C_6$)alkylcarbonyl radical; an N,N-di($C_1$–$C_6$)alkylamino($C_1$–$C_6$) alkylcarbonyl radical; a carbamyl radical; an N—($C_1$–$C_6$)alkylcarbamyl radical; an N,N-di($C_1$–$C_6$) alkylcarbamyl radical; a thiocarbamyl radical; an aminosulphonyl radical; an N—Z-aminosulphonyl radical; an N—($C_1$–$C_6$)alkylaminosulphonyl radical; an N,N-di($C_1$–$C_6$)alkylaminosulphonyl radical; a ($C_1$–$C_6$) alkylsulphonyl radical; a group —CO—Z or a group —CO—OZ;

Z represents a group of formula (II) below:

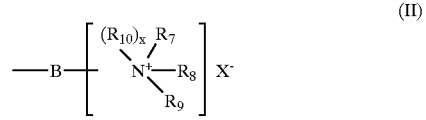

(II)

in which:
B is a linker arm which represents a linear or branched alkyl chain preferably containing from 1 to 14 carbon atoms, which may be interrupted by one or more hetero atoms such as oxygen, sulphur or nitrogen atoms, and which may be substituted with one or more hydroxyl or $C_1$–$C_6$ alkoxy radicals;

$R_7$, $R_8$ and $R_9$, which may be identical or different, represent a $C_1$–$C_6$ alkyl radical; a $C_1$–$C_6$ monohydroxyalkyl radical; a $C_2$–$C_6$ polyhydroxyalkyl radical; a ($C_1$–$C_6$)alkoxy($C_1$–$C_6$)alkyl radical; a cyano($C_1$–$C_6$)alkyl radical; an aryl radical; a benzyl radical; a carbamyl($C_1$–$C_6$)alkyl radical; a tri($C_1$–$C_6$)alkylsilane($C_1$–$C_6$)alkyl radical or a $C_1$–$C_6$ aminoalkyl radical in which the amine is protected with a ($C_1$–$C_6$)alkylcarbonyl, carbamyl or ($C_1$–$C_6$)alkylsulphonyl radical; two of the radicals $R_7$, $R_8$ and $R_9$ can also form, together with the nitrogen atom to which they are attached, a 5- or 6-membered saturated carbon-based ring or a ring containing one or more hetero atoms such as, for example, a pyrrolidone ring, a piperidine ring, a piperazine ring or a morphotine ring, it being possible for the said ring to be unsubstituted or substituted with a halogen atom, a hydroxyl radical, a $C_1$–$C_6$ alkyl radical, a $C_1$–$C_6$ monohydroxyalkyl radical, a $C_2$–$C_6$ polyhydroxyalkyl radical, a nitro radical, a cyano radical, a cyano($C_1$–$C_6$)alkyl radical, a $C_1$–$C_6$ alkoxy radical, a tri($C_1$–$C_6$)alkylsilane($C_1$–$C_6$)alkyl radical, an amido radical, an aldehyde radical, a carboxyl radical, a ($C_1$–$C_6$)alkylcarbonyl radical, a thio radical, a $C_1$–$C_6$ thioalkyl radical, a ($C_1$–$C_6$)alkylthio radical, an amino radical, an amino radical protected with a ($C_1$–$C_6$)alkylcarbonyl, carbamyl or ($C_1$–$C_6$)alkylsulphonyl radical; one of the radicals $R_7$, $R_8$ and $R_9$ can also represent a linker arm B' of a second radical Z, B' having the same meaning as that given above for the radical B;

$X^-$ represents a monovalent or divalent anion and is preferably chosen from a halogen atom such as chlorine, bromine, fluorine or iodine, a hydroxide, a hydrogen sulphate or a $C_1$–$C_6$ alkyl sulphate such as, for example, a methyl sulphate or an ethyl sulphate;

$R_{10}$ represents a $C_1$–$C_6$ alkyl radical; a $C_1$–$C_6$ monohydroxyalkyl radical; a $C_2$–$C_6$ polyhydroxyalkyl radical; an aryl radical; a benzyl radical; a $C_1$–$C_6$ aminoalkyl radical, a $C_1$–$C_6$ aminoalkyl radical in which the amine is protected with a ($C_1$–$C_6$) alkylcarbonyl, carbamyl or $C_1$–$C_6$ alkylsulphonyl radical; a carboxy($C_1$–$C_6$)alkyl radical; a cyano($C_1$–$C_6$)alkyl radical; a carbamyl($C_1$–$C_6$)alkyl radical; a $C_1$–$C_6$ trifluoroalkyl radical; a tri($C_1$–$C_6$)alkylsilane($C_1$–$C_6$)alkyl radical; a $C_1$–$C_6$ sulphonamidoalkyl radical; a ($C_1$–$C_6$)alkylcarboxy($C_1$–$C_6$)alkyl radical; a ($C_1$–$C_6$)alkylsulphinyl($C_1$–$C_6$)alkyl radical; a ($C_1$–$C_6$)alkylsulphonyl($C_1$–$C_6$)alkyl radical; a ($C_1$–$C_6$)alkylketo($C_1$–$C_6$) alkyl radical; an N—($C_1$–$C_6$)alkylcarbamyl($C_1$–$C_6$) alkyl radical; an N—($C_1$–$C_6$)alkylsulphonamido ($C_1$–$C_6$)alkyl radical;

x is an integer equal to 0 or 1; with the following conditions:
when x=0, then the linker arm B is attached to the nitrogen atom bearing the radicals $R_7$ to $R_9$;
when x=1, then two of the radicals $R_7$ to $R_9$ form, together with the nitrogen atom to which they are attached, a saturated 5- or 6-membered ring as defined above, and the linker arm B is borne by a carbon atom of the said saturated ring;

it being understood that:
the number of groups Z is at least equal to 1;
when the compounds of formula (I) comprise only one group Z, and when A1 and A2 respectively denote —$NR_4R_5$ and —$NR'_4R'_5$ in which:
either the radicals $R_4$ and $R_5$, which may be identical or different, represent a hydrogen atom or a $C_1$–$C_6$ alkyl or $C_1$–$C_6$ hydroxyalkyl radical, and the radicals $R'_4$ and $R'_5$ simultaneously represent a hydrogen atom,
or $R_4$ and $R_5$ simultaneously represent a hydrogen atom and the radicals $R'_4$ and $R'_5$, which may be identical or different, represent a hydrogen atom or a $C_1$–$C_6$ alkyl or $C_1$–$C_6$ hydroxyalkyl radical, and when one and only one of the radicals $R_1$ to $R_3$ represents a group $OR_6$ in which $R_6$ represents a group Z in which the linker arm B is a $C_3$ alkyl chain monosubstituted in position 2 with a hydroxyl radical and in which the radicals $R_7$, $R_8$ and $R_9$, which may be identical or different, represent a $C_1$–$C_6$ alkyl or $C_1$–$C_6$ hydroxyalkyl radical or together form, with the nitrogen atom to which they are attached, a morpholine or piperidine ring, then the other two radicals $R_1$ to $R_3$ cannot simultaneously denote a hydrogen atom; and with the exclusion of:

ethyl(2-hydroxyethyl)dimethylammonium 4-(methylamino) salicylate bromide;
3-[(4-amino-2-hydroxybenzoyl)oxy]-N-ethyl-N,N-dimethyl-1-propanaminium iodide;
3-[(4-amino-2-hydroxybenzoyl)oxy]-N,N,N-trimethyl-1-propaniminium iodide;
triethyl(2-hydroxyethyl)ammonium 4-aminosalicylate bromide;
2-[(4-amino-2-hydroxybenzoyl)oxy]-N,N-diethyl-N-methylethanaminium iodide;
2-[(4-amino-2-hydroxybenzoyl)oxy]-N-ethyl-N,N-dimethylethanaminium iodide;
ethyl(2-hydroxyethyl)dimethylammonium-4-aminosalicylate bromide;
2-[(4-amino-2-hydroxybenzoyl)oxy]-N,N,N-trimethylethanaminium iodide;
2-[(4-amino-2-hydroxybenzoyl)oxy]-N,N,N-trimethylethanaminium chloride;
trimethyl[(3-dipropylaminophenylcarbamoyl)methyl] ammonium chloride;
trimethyl[(3-dimethylamino-4-methoxyphenylcarbamoyl) methyl]ammonium methosulphate;
trimethyl[(3-di-β-hydroxyethylaminophenylcarbamoyl) methyl]ammonium ethosulphate;
trimethyl[(3-aminophenylcarbamoyl)methyl]ammonium iodide;,
diethylmethyl[(3-aminophenylcarbamoyl)methyl] ammonium iodide;
benzyldiethyl[(3-aminophenylcarbamoyl)methyl] ammonium chloride;
trimethyl[(3,5-dihydroxyphenylcarbamoyl)ethyl] ammonium iodide;
2-[(3,5-dihydroxybenzoyl)oxy]-N,N,N-trimethylethanaminium; and 2-[(2,6-dihydroxybenzoyl)oxy]-N,N,N-trimethylethanaminium;

these compounds being known for their pharmacodynamic or antiseptic properties, or as synthetic intermediates (see in particular Chemical Abstract (C.A.) 75, 48628; C.A. 51, 1464; C.A. 88, 34348; H. von Heuler et al. Vol. No. 2, No. 14, (1951), Pages 297–302; Clausen et al., (1983), 260(1), 193-9; J. Thomas et al., J. Pharm. Pharmacol., Vol. 13, (1961), pages 129–138; BE 639 047; DE 964 053; EP 0 241 915).

Among the compounds of formula (I') above which may be mentioned in particular, are:

[2-(2,4-diaminophenoxy)ethyl]diethylmethylammonium chloride;
1-[3-(2,4-diaminophenoxy)propyl]-1,4-dimethylpiperazin-1-ium chloride;
1-[(3-hydroxy-4-methylphenylcarbamoyl)methyl]-1,4-dimethylpiperazin-1-ium chloride;
1,4-bis(2-hydroxyethyl)-1-[(3-hydroxyphenylcarbamoyl)methyl]piperazin-1-ium chloride;
[3-(2,4-diaminophenoxy)propyl]triethylammonium chloride;
1-[(2,4-dihydroxyphenylcarbamoyl)methyl]-1-methylpiperidinium chloride;
[2-(2,4-dihydroxyphenyl)-2-oxoethyl]triethylammonium chloride;
1-[(3-hydroxy-4-methylphenylcarbamoyl)methyl]-1-methylpyrrolidinium chloride;
1-[(2,6-dihydroxyphenylcarbamoyl)methyl]-1-methylpyrrolidinium chloride;
[2-(4-amino-2-hydroxyphenoxy)ethyl]diethylmethylammonium chloride;
triethyl [2-(3-hydroxy-4-methylphenylamino)ethyl] ammonium bromide;
1-[2-(3-hydroxy-4-methylphenylamino)ethyl]-1,4-dimethylpiperazin-1-ium bromide;
4-[(3-hydroxyphenylcarbamoyl)methyl]-4-methylmorpholin-4-ium chloride;
triethyl[2-(3-hydroxy-2,4-dimethylphenylcarbamoyloxy)ethyl]ammonium chloride;
[2-(4-chloro-3-hydroxyphenylamino)ethyl] triethylammonium bromide;
1-[3-(2-amino-4-methylaminophenoxy)propyl]-1-methylpiperidinium chloride;
[2-(2,4-diaminophenoxy)ethyl]diethylmethylammonium chloride;
1-(3-trimethylammonium-2-hydroxypropyl)-1-[(3-hydroxy-4-methylphenylcarbamoyl)methyl]pyrrolidinium dichloride;
1-[2-(3-amino-4-methoxyphenylamino)ethyl]-1,4-dimethylpiperazin-1-ium bromide;
[2-(2,4-diaminophenyl)ethyl]triethylammonium chloride;
1-[(3-hydroxy-2,4-dimethylphenylcarbamoyl)methyl]-1,4-dimethylpiperazin-1-ium chloride;
N,N-bis[2-(1-methylpyrrolidinium)ethyl]benzene-1,3-diamine dichloride;
triethyl[(3-hydroxy-4-methylphenylcarbamoyl)methyl] ammonium chloride;
N,N'-bis{2-[1,4-bis(2-hydroxyethyl)piperazin-1-ium] ethyl}benzene-1,3-diamine-2-methyl dichloride;
1-[3-(2,4-diaminophenoxy)propyl]-1-methylpyrrolidinium chloride;
1-[(3-hydroxyphenylcarbamoyl)methyl]-1,4-dimethylpiperazin-1-ium chloride;
1-[3-(2,4-diaminophenoxy)propyl]-4-(3-trimethylammonium-2-hydroxypropyl)-1,4-dimethylpiperazine-1,4-diium trichloride;

and the addition salts thereof with an acid.

The compounds of formula (I') in accordance with the invention can be readily obtained, according to methods that are well known in the prior art, for example by reducing the corresponding cationic nitro compounds (cationic meta-nitroanilines or cationic meta-nitrophenols).

This reduction step (production of a primary aromatic amine), optionally followed by a salification, is generally, for convenience, the last step of the synthesis.

This reduction can take place earlier in the sequence of reactions leading to the preparation of the compounds of formula (I'), and according to processes that are well known; in this case, it is necessary to "protect" the primary amine created (for example by means of a step of acetylation, benzenesulphonation, etc.), then carry out the desired substitution(s) or modification(s) (including the quaternization) and end with the "deprotection" (generally in acidic medium) of the amine function.

Similarly, the phenolic function can be protected according to methods that are well known, with a benzyl radical ("deprotection" by catalytic reduction) or with an acetyl or mesyl radical ("deprotection" in acidic medium).

When the synthesis is complete, the compounds of formula (I') in accordance with the invention can, if necessary, be recovered by methods that are well known in the prior art, such as crystallization or distillation.

Another subject of the invention is the use of the compounds of formula (I) or of formula (I'), in accordance with the invention, as couplers for the oxidation dyeing of keratin fibres, and in particular of human keratin fibres such as the hair.

The examples which follow are intended to illustrate the invention without thereby limiting its scope.

PREPARATION EXAMPLES

Example 1

Preparation of [2-(2,4-diaminophenoxy)ethyl] diethylmethylammonium chloride dihydrochloride

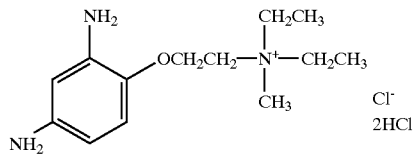

a) Synthesis of N-[2-(2-diethylaminoethoxy)-5-nitrophenyl]acetamide

A suspension of 35.1 g (0.15 mol) of the potassium salt of N-(2-hydroxy-5-nitrophenyl)acetamide and 23.0 g (0.17 mol) of (2-chloroethyl)diethylamine in 105 ml of dimethylformamide was heated on a boiling water bath.

The mixture was poured into 450 ml of ice-cold water containing a small amount of sodium hydroxide, and the crystalline precipitate was spin-filtered, reslurried in water and dried under vacuum at 45° C. over phosphorus pentoxide.

After recrystallization from refluxing methanol, pale yellow crystals (22.8 g) of N-[2-(2-diethylaminoethoxy)-5-nitrophenyl]acetamide were obtained, which melted at 116° C. and the elemental analysis of which, calculated for $C_{14}H_{21}N_3O_4$, was:

| % | C | H | N |
|---|---|---|---|
| Calculated | 56.94 | 7.17 | 14.23 |
| Found | 57.15 | 7.47 | 14.35 | b) Synthesis of [2-(2,4-bisacetylaminophenoxy) ethyl]diethylmethylammonium iodide 15.0 g (0.05 mol) of N-[2-(2-diethylaminoethoxy)-5-nitrophenyl]acetamide obtained above in the preceding step, 1 g of 5% palladium-on-charcoal (containing 50% water) and 60 ml of ethanol were placed in a hydrogenator.

The reduction was carried out over ½ an hour under hydrogen pressure of about 8 bar and at a temperature which was gradually raised to 80° C. After filtering off the catalyst under nitrogen, the filtrate was evaporated to dryness under reduced pressure, taken up in 45 ml of dioxane and acetylated with 6 g of acetic anhydride. The white precipitate was spin-filtered, washed in dioxane and dried under vacuum at 50° C. 15.3 g of white crystals of N-[5-acetylamino-2-(2-diethylaminoethoxy)phenyl]acetamide were obtained, and were dissolved in 150 ml of refluxing acetone. Quaternization was carried out by adding 10.6 g (0.075 mol) of methyl iodide dropwise.

Stirring was carried out for 10 minutes, and the white precipitate obtained was spin-filtered, washed with boiling acetone and dried under vacuum at 45° C.

21.0 g of white crystals of [2-(2,4-bisacetylaminophenoxy)ethyl]diethylmethylammonium iodide were obtained, the elemental analysis of which, calculated for $C_{17}H_{28}N_3O_3I$, was:

| % | C | H | N | O | I |
|---|---|---|---|---|---|
| Calculated | 45.44 | 6.28 | 9.35 | 10.68 | 28.24 |
| Found | 45.34 | 6.25 | 9.32 | 10.83 | 28.28 | c) Deacetylation of [2-(2,4-bisacetylaminophenoxy) ethyl]diethylmethylammonium iodide 21.0 g (0.0467 mol) of [2-(2,4-bisacetylaminophenoxy) ethyl]diethylmethylammonium iodide obtained above in the preceding step in 35 ml of 36% hydrochloric acid and 35 ml of ethanol were refluxed for one hour.

The solution was cooled and diluted with 100 ml of ethanol.

The white precipitate was spin-filtered, washed with acetone and dried under vacuum at 50° C. over potassium hydroxide.

11.7 g of white crystals of [2-(2,4-diaminophenoxy)ethyl] diethylmethylammonium chloride dihydrochloride were obtained, the elemental analysis of which, calculated for $C_{13}H_{26}N_3OCl_3$, was:

| % | C | H | N | O | Cl |
|---|---|---|---|---|---|
| Calculated | 45.03 | 7.56 | 12.12 | 4.61 | 30.67 |
| Found | 44.86 | 7.51 | 12.03 | 4.70 | 30.83 |

Example 2

Preparation of 1-[3-(2,4-diaminophenoxy)propyl]-1, 4-dimethylpiperazin-1-ium trihydrochloride dihydrate

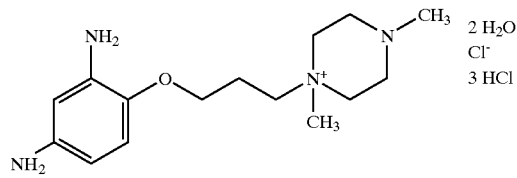

a) Synthesis of N-[2-(3-chloropropoxy)-5-nitrophenyl]acetamide 708.5 g (4.5 mol) of 1-bromo-3-chloropropane were added over 50 minutes to a suspension of 294.2 g (1.5 mol) of N-(2-hydroxy-5-nitrophenyl)acetamide and 228.0 g (1.65 mol) of potassium carbonate in 900 ml of dimethylformamide, stirred at room temperature.

The orange-coloured suspension was stirred for 4 hours at room temperature and then for 2 hours at 28–30° C.

The reaction mixture was poured into 4 litres of ice-cold water; an oil precipitated out.

This oil was separated out after settling of the phases and taken up in 500 ml of isopropanol; the crystals obtained were spin-filtered and recrystallized from refluxing isobutanol.

Pale yellow crystals (84.4 g) of N-[2-(3-chloropropoxy)-5-nitrophenyl]acetamide were obtained, which melted at 130° C. (Kofler) and the elemental analysis of which, calculated for $C_{11}H_{13}N_2O_4Cl$, was:

| % | C | H | N | O | Cl |
|---|---|---|---|---|---|
| Calculated | 48.45 | 4.81 | 10.27 | 23.47 | 13.00 |
| Found | 48.05 | 4.82 | 10.16 | 23.33 | 12.60 | b) Synthesis of 1-[3-(2-acetylamino-4-nitrophenoxy)propyl]-1,4-dimethylpiperazin-1-ium chloride A solution of 81.8 g (0.3 mol) of N-[2-(3-chloropropoxy)-5-nitrophenyl]acetamide obtained above in the preceding step and 62.8 g (0.55 mol) of 1,4-dimethylpiperazine were refluxed in isobutanol (300 ml) for 25 hours.

The crystalline quaternized compound precipitated out; it was spin-filtered, washed with absolute ethanol and recrystallized from refluxing 96° ethanol.

Pale yellow crystals (55.0 g) of 1-[3-(2-acetylamino-4-nitrophenoxy)propyl]-1,4-dimethylpiperazin-1-ium chloride were obtained, which melted at 214° C. (Kofler) and the elemental analysis of which, calculated for $C_{17}H_{29}N_4O_2Cl.1/2H_2O$, was:

| % | C | H | N | O | Cl |
|---|---|---|---|---|---|
| Calculated | 51.58 | 7.13 | 14.15 | 18.19 | 8.96 |
| Found | 51.46 | 7.05 | 13.88 | 17.44 | 8.80 | c) Synthesis of 1-[3-(2-acetylamino-4-aminophenoxy)propyl]-1,4-dimethylpiperazin-1-ium chloride 55.0 g (0.142 mol) of 1-[3-(2-acetylamino-4-nitrophenoxy)propyl]-1,4-dimethylpiperazin-1-ium chloride obtained above in the preceding step, 10 g of 5% palladium-on-charcoal (containing 50% water), 300 ml of water and 300 ml of isopropanol were placed in a hydrogenator.

The reduction took place in ½ an hour under a hydrogen pressure of about 9 bar and at a temperature which was gradually raised to 70° C. After filtering off the catalyst under nitrogen, the filtrate was evaporated to dryness under reduced pressure (crystals).

The product was recrystallized from refluxing 96° ethanol and white crystals of 1-[3-(2-acetylamino-4-aminophenoxy) propyl]-1,4-dimethylpiperazin-1-ium (28.0 g) were obtained, which melted at 226° C. (Kofler) and the elemental analysis of which, calculated for $C_{17}H_{29}N_4O_2Cl.1/2H_2O$, was:

| % | C | H | N | O | Cl |
|---|---|---|---|---|---|
| Calculated | 55.80 | 8.26 | 15.31 | 10.93 | 9.69 |
| Found | 55.84 | 8.08 | 15.26 | 10.28 | 9.63 | d) Deacetylation of 1-[3-(2-acetylamino-4-aminophenoxy)propyl]-1,4-dimethylpiperazin-1-ium chloride 28.0 g (0.0784 mol) of 1-[3-(2-acetylamino-4-aminophenoxy)propyl]-1,4-dimethylpiperazin-1-ium chloride obtained above in the preceding step, in 50 ml of 36% hydrochloric acid and 100 ml of ethanol, were refluxed for two hours.

The solution was cooled; the precipitated gum was separated out and taken up in absolute ethanol (crystallization).

The product was spin-filtered and recrystallized from a refluxing mixture of ethanol/36% hydrochloric acid.

White crystals of 1-[3-(2,4-diaminophenoxy)propyl]-1,4-dimethylpiperazin-1-ium chloride trihydrochloride dihydrate (24.9 g) were obtained, which melted with decomposition at 255–260° C. (Kofler), the 1H NMR structure of which was in accordance with the expected product, and the elemental analysis of which, calculated for $C_{15}H_{13}N_4OCl_4.2H_2O$, was:

| % | C | H | N | O | Cl |
|---|---|---|---|---|---|
| Calculated | 39.14 | 7.85 | 12.17 | 10.43 | 30.81 |
| Found | 39.02 | 7.56 | 11.85 | 10.72 | 30.45 |

APPLICATION EXAMPLES

Examples 1 to 3 of Dyeing in Basic Medium

The dye compositions below were prepared (contents in grams):

| EXAMPLE | 1 | 2 | 3 |
|---|---|---|---|
| [2-(2,4-Diaminophenoxy)ethyl]diethyl-methylammonium chloride dihydrochloride (compound of formula (I)) | 1.04 | 0.693 | 0.693 |
| para-Aminophenol (oxidation base) | 0.327 | — | — |
| para-Phenylenediamine (oxidation base) | — | 0.216 | — |
| 4,5-Diamino-1-ethyl-3-methylpyrazole dihydrochloride (oxidation base) | — | — | 0.426 |
| Common dye support No. 1 | (*) | (*) | (*) |
| Demineralized water qs | 100 g | 100 g | 100 g |

(*) Common dye support No. 1:

| | |
|---|---|
| Benzyl alcohol | 2 g |
| Polyethylene glycol containing 6 mol of ethylene oxide | 3 g |
| 96° ethanol | 18 g |
| $(C_8-C_{10})$alkylpolyglucoside as an aqueous solution containing 60% active material (A.M.), buffered with ammonium citrate, sold under the name Oramix CG110 ® by the company SEPPIC | 6 g |
| Aqueous ammonia containing 20% $NH_3$ | 10 g |
| Sodium metabisulphite | 0.23 g |
| Sequestering agent | qs |

At the time of use, the dye composition of Example 1 above was mixed, weight for weight, with a 20-volumes hydrogen peroxide solution (6% by weight) of pH 3.

At the time of use, each of the dye compositions of Examples 2 and 3 above were mixed, weight for weight, with an oxidizing composition consisting of an aqueous ammonium persulphate solution at a concentration of $6.10^{-3}$ mol %.

Each of the mixtures obtained was applied to locks of natural or permanent-waved grey hair containing 90% white hairs, for 30 minutes. The locks were then rinsed, washed with a standard shampoo, rinsed again and then dried.

The shades obtained are given in the table below:

| EXAMPLE | DYEING pH | Shade on natural hair | Shade on permanent-waved hair |
|---|---|---|---|
| 1 | 10 ± 0.2 | Slightly ash iridescent | Violet iridescent |
| 2 | 10 ± 0.2 | Ash-blue | Deep blue |
| 3 | 10 ± 0.2 | Ash-violet | Strong violet |

Example 4 of Dyeing in Acidic Medium

The dye composition below was prepared:

| | |
|---|---|
| [2-(2,4-Diaminophenoxy)ethyl]diethyl-methylammonium chloride dihydrochloride (compound of formula (I)) | 0.693 g |
| para-Tolylenediamine (oxidation base) | 0.244 g |
| Benzyl alcohol | 2 g |
| Polyethylene glycol containing 6 mol of ethylene oxide | 3 g |
| 96° ethanol | 18 g |
| $(C_8-C_{10})$alkylpolyglucoside as an aqueous solution containing 60% active material (A.M.), buffered with ammonium citrate, sold under the name Oramix CG110 ® by the company SEPPIC | 6 g |
| $K_2HPO_4/KH_2PO_4$ (1.5 M/1 M) buffer | 10 g |

-continued

| The dye composition below was prepared: | |
|---|---|
| Sodium metabisulphite | 0.23 g |
| Sequestering agent | qs |
| Demineralized water qs | 100 g |

At the time of use, the above dye composition was mixed, weight for weight, with a 20-volumes hydrogen peroxide solution (6% by weight) of pH 3.

The mixture obtained was applied to locks of natural or permanent-waved grey hair, containing 90% white hairs, for 30 minutes. The locks were then rinsed, washed with a standard shampoo, rinsed again and then dried.

The shades obtained are given in the table below:

| EXAMPLE | DYEING pH | Shade on natural hair | Shade on permanent-waved hair |
|---|---|---|---|
| 4 | 5.7 ± 0.2 | Blue-ash | Strong blue-ash |

Example 5 of Enzymatic Dyeing

| The dye composition below was prepared: | |
|---|---|
| [2-(2,4-Diaminophenoxy)ethyl]diethyl-methylammonium chloride dihydrochloride (compound of formula (I)) | 1.04 g |
| para-Phenylenediamine (oxidation base) | 0.324 g |
| Propylene glycol monomethyl ether | 10 g |
| Crosslinked acrylic acid/($C_{10}$/$C_{30}$)alkyl acrylate copolymer | 0.25 g |
| Lauryl alcohol oxyethylenated with 12 mol of ethylene oxide | 2 g |
| Uric acid | 1 g |
| Uricase from Arthrobacter globiformis at a concentration of 20 International Units (I.U.)/mg, sold by the company SIGMA | 1 g |
| Antioxidant | 0.1 g |
| 2-Amino-2-methyl-1-propanol qs | pH 9.5 |
| Demineralized water qs | 100 g |

The above dye composition was applied for 30 minutes to 20 mg samples of natural or permanent-waved grey hair containing 90% white hairs. The hair was then rinsed, washed with shampoo, rinsed again and then dried.

The shades obtained are given in the table below:

| EXAMPLE | Shade on natural hair | Shade on permanent-waved hair |
|---|---|---|
| 5 | Slightly ashen strong blue | Slightly ashen strong blue |

What is claimed is:

1. A composition for oxidation dyeing of keratin fibres comprising, in a medium suitable for dyeing, at least one coupler chosen from monobenzenic couplers of formula (I) and the acid addition salts thereof:

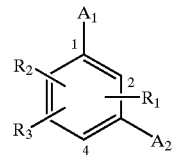

(I)

wherein:

$R_1$, $R_2$ and $R_3$, which may be identical or different, are each chosen from hydrogen atoms, halogen atoms, groups Z as defined below, groups —CO—Z, group —CO—OZ, ($C_1$-$C_6$)alkylcarbonyl groups, amino ($C_1$-$C_8$)alkylcarbonyl groups, N—Z-amino($C_1$-$C_6$) alkylcarbonyl groups, N—($C_1$-$C_6$)alkylamino($C_1$-$C_6$) alkylcarbonyl groups, N,N-di($C_1$-$C_6$)alkylamino ($C_1$-$C_6$)alkylcarbonyl groups, amino($C_1$-$C_6$) alkylcarbonyl($C_1$-$C_6$)alkyl groups, N—Z-amino ($C_1$-$C_6$)alkylcarbonyl($C_1$-$C_6$)alkyl groups, N—($C_1$-$C_6$)alkylamino($C_1$-$C_6$)alkylcarbonyl($C_1$-$C_6$) alkyl groups, N,N-di($C_1$-$C_6$)alkylamino($C_1$-$C_6$) alkylcarbonyl($C_1$-$C_6$)alkyl groups, carboxyl groups, ($C_1$-$C_6$)alkylcarboxyl groups, $C_1$-$C_6$ alkylsulphonyl groups, aminosulphonyl groups, N—Z-aminosulphonyl groups, $C_1$-$C_6$ N-alkylaminosulphonyl groups, N,N-di($C_1$-$C_6$) alkylaminosulphonyl groups, $C_1$-$C_6$aminosulphonylalkyl groups, $C_1$-$C_6$ N—Z-aminosulphonylalkyl groups, N—($C_1$-$C_6$) alkylaminosulphonyl($C_1$-$C_6$)alkyl groups, N,N-di ($C_1$-$C_6$)alkylaminosulphonyl($C_1$-$C_6$)alkyl groups, carbamyl groups, N-($C_1$-$C_6$)alkylcarbamyl groups, N,N-di($C_1$-$C_6$)alkylcarbamyl groups, carbamyl ($C_1$-$C_6$)alkyl groups, N—($C_1$-$C_6$)alkylcarbamyl ($C_1$-$C_6$)alkyl groups, N,N-di($C_1$-$C_6$)alkylcarbamyl ($C_1$-$C_6$)alkyl groups, $C_1$-$C_6$ alkyl groups, $C_1$-$C_6$ monohydroxyalkyl groups, $C_2$-$C_6$ polyhydroxyalkyl groups, ($C_1$-$C_6$)alkoxy($C_1$-$C_6$)alkyl groups, $C_1$-$C_6$ trifluoroalkyl groups, cyano groups, groups $OR_6$, groups $R_6$ and amino groups protected with at least one group chosen from ($C_1$-$C_6$)alkylcarbonyl groups, ($C_1$-$C_6$) alkylcarboxyl groups, trifluoro($C_1$-$C_6$)alkylcarbonyl groups, amino($C_1$-$C_6$)alkylcarbonyl groups, N—Z-amino($C_1$-$C_6$)alkylcarbonyl groups, N—($C_1$-$C_6$) alkylamino($C_1$-$C_6$)alkylcarbonyl groups, N,N-di ($C_1$-$C_6$)alkylamino($C_1$-$C_6$)alkylcarbonyl groups, ($C_1$-$C_6$)alkylcarboxyl groups, carbamyl groups, N—($C_1$-$C_6$)alkylcarbamyl groups, N,N-di($C_1$-$C_6$) alkylcarbamyl groups, $C_1$-$C_6$ alkylsulphonyl groups, aminosulphonyl groups, N—Z-aminosulphonyl groups, $C_1$-$C_6$ N-alkylaminosulphonyl groups, N,N-di ($C_1$-$C_6$)alkylaminosulphonyl groups, thiocarbamyl groups, formyl groups, groups —CO—Z and groups —CO—OZ; wherein:

$R_6$, which may be identical or different, are each chosen from $C_1$-$C_6$ alkyl groups, $C_1$-$C_6$ monohydroxyalkyl groups, $C_2$-$C_6$ polyhydroxyalkyl groups, groups Z as defined below, ($C_1$-$C_6$)alkoxy($C_1$-$C_6$)alkyl groups, aryl groups, benzyl groups, carboxy($C_1$-$C_6$) alkyl groups, ($C_1$-$C_6$)alkylcarboxy($C_1$-$C_6$)alkyl groups, cyano($C_1$-$C_6$)alkyl groups, carbamyl ($C_1$-$C_6$)alkyl groups, N—($C_1$-$C_6$)alkylcarbamyl ($C_1$-$C_6$)alkyl groups, N,N-di($C_1$-$C_6$)alkylcarbamyl ($C_1$-$C_6$)alkyl groups, $C_1$-$C_6$ trifluoroalkyl groups, $C_1$-$C_6$ aminosulphonylalkyl groups, $C_1$-$C_6$ N—Z-aminosulphonylalkyl groups, N—($C_1$-$C_6$)

alkylaminosulphonyl($C_1$–$C_6$)alkyl groups, N,N-di($C_1$–$C_6$)alkylaminosulphonyl($C_1$–$C_6$)alkyl groups, ($C_1$–$C_6$)alkylsulphinyl($C_1$–$C_6$)alkyl groups, ($C_1$–$C_6$)alkylsulphonyl($C_1$–$C_6$)alkyl groups, ($C_1$–$C_6$)alkylcarbonyl($C_1$–$C_6$)alkyl groups, $C_1$–$C_6$ aminoalkyl groups and $C_1$–$C_6$ aminoalkyl groups wherein said amino group is substituted with one or two groups, which may be identical or different, each chosen from $C_1$–$C_6$ alkyl groups, $C_1$–$C_6$ monohydroxyalkyl groups, $C_2$–$C_6$ polyhydroxyalkyl groups, ($C_1$–$C_6$)alkylcarbonyl groups, formyl groups, trifluoro-($C_1$–$C_6$)alkylcarbonyl groups, ($C_1$–$C_6$)alkylcarboxyl groups, carbamyl groups, N—($C_1$–$C_6$)alkylcarbamyl groups, N,N-di($C_1$–$C_6$)alkylcarbamyl groups, thiocarbamyl groups, $C_1$–$C_6$ alkylsulphonyl groups, groups Z, groups —CO—Z and groups —CO—OZ;

$A_1$ is chosen from groups —$NR_4R_5$ and hydroxyl groups, wherein $R_4$ and $R_5$ are as defined below; and $A_2$ is chosen from groups —$NR'_4R'$, and hydroxyl groups, wherein:

$R_4$, $R'_4$, $R_5$ and $R'_5$, which may be identical or different, are each chosen from hydrogen atoms, groups Z as defined below, $C_1$–$C_6$ alkyl groups, $C_1$–$C_6$ monohydroxyalkyl groups, $C_2$–$C_6$ polyhydroxyalkyl groups, ($C_1$–$C_6$)alkoxy($C_1$–$C_6$)alkyl groups, aryl groups, benzyl groups, cyano($C_1$–$C_6$)alkyl groups, carbamyl($C_1$–$C_6$)alkyl groups, N—($C_1$–$C_6$)alkylcarbamyl($C_1$–$C_6$)alkyl groups, N,N-di($C_1$–$C_6$)alkylcarbamyl($C_1$–$C_6$)alkyl groups, thiocarbamyl($C_1$–$C_6$)alkyl groups, $C_1$–$C_6$ trifluoroalkyl groups, $C_1$–$C_6$ sulphoalkyl groups, ($C_1$–$C_6$)alkylcarboxy($C_1$–$C_6$)alkyl groups, ($C_1$–$C_6$)alkylsulphinyl($C_1$–$C_6$)alkyl groups, $C_1$–$C_6$ aminosulphonylalkyl groups, $C_1$–$C_6$ N—Z-aminosulphonylalkyl groups, N—($C_1$–$C_6$)alkylaminosulphonyl($C_1$–$C_6$)alkyl groups, N,N-di($C_1$–$C_6$)alkylaminosulphonyl($C_1$–$C_6$)alkyl groups, ($C_1$–$C_6$)alkylcarbonyl($C_1$–$C_6$)alkyl groups, $C_1$–$C_6$ aminoalkyl groups, $C_1$–$C_6$ aminoalkyl groups wherein said amino group is substituted with one or two groups, which may be identical or different, each chosen from $C_1$–$C_6$ alkyl groups, $C_1$–$C_6$ monohydroxyalkyl groups, $C_2$–$C_6$ polyhydroxyalkyl groups, ($C_1$–$C_6$)alkylcarbonyl groups, carbamyl groups, N—($C_1$–$C_6$)alkylcarbamyl groups, N,N-di($C_1$–$C_6$)alkylcarbamyl groups, $C_1$–$C_6$ alkylsulphonyl groups, formyl groups, trifluoro($C_1$–$C_6$)alkylcarbonyl groups, ($C_1$–$C_6$)alkylcarboxyl groups, thiocarbamyl groups, groups Z, groups —CO—Z and groups —CO—OZ, wherein:

one of said $R_4$, $R'_4$, $R_5$ and $R'_5$, which may be identical or different, may optionally also be chosen from ($C_1$–$C_6$)alkylcarboxyl groups, ($C_1$–$C_6$)alkylcarbonyl groups, formyl groups, trifluoro($C_1$–$C_6$)alkylcarbonyl groups, amino($C_1$–$C_6$)alkylcarbonyl groups, N—Z-amino($C_1$–$C_6$)alkylcarbonyl groups, N—($C_1$–$C_6$)alkylamino($C_1$–$C_6$)alkylcarbonyl groups, N,N-di($C_1$–$C_6$)alkylamino($C_1$–$C_6$)alkylcarbonyl groups, carbamyl groups, N—($C_1$–$C_6$)alkylcarbamyl groups, N,N-di($C_1$–$C_6$)alkylcarbamyl groups, thiocarbamyl groups, aminosulphonyl groups, N—Z-aminosulphonyl groups, N—($C_1$–$C_6$)alkylaminosulphonyl groups, N,N-di($C_1$–$C_6$)alkylaminosulphonyl groups, ($C_1$–$C_6$)alkylsulphonyl groups, groups —CO—Z and groups —CO—OZ;

groups Z, which may be identical or different, are each chosen from groups of formula (II):

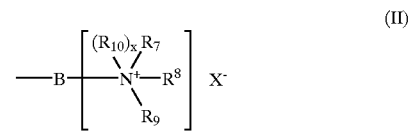

wherein:

B is a linker arm chosen from linear and branched divalent alkyl groups, which are optionally interrupted by at least one heteroatom and which are optionally substituted with at least one group chosen from hydroxyl groups and $C_1$–$C_6$ alkoxy groups;

$R_7$, $R_8$ and $R_9$, which may be identical or different, are each chosen from $C_1$–$C_6$ alkyl groups, $C_1$–$C_6$ monohydroxyalkyl groups, $C_2$–$C_6$ polyhydroxyalkyl groups, ($C_1$–$C_6$)alkoxy($C_1$–$C_6$)alkyl groups, cyano($C_1$–$C_6$)alkyl groups, aryl groups, benzyl groups, carbamyl($C_1$–$C_6$)alkyl groups, N—($C_1$–$C_6$)alkylcarbamyl($C_1$–$C_6$)alkyl groups, tri($C_1$–$C_6$)alkylsilane($C_1$–$C_6$)alkyl groups and $C_1$–$C_6$ aminoalkyl groups wherein said amino group is protected with at least one group chosen from ($C_1$–$C_6$)alkylcarbonyl groups, carbamyl groups and ($C_1$–$C_6$)alkylsulphonyl groups, wherein:

two of said $R_7$, said $R_8$ and said $R_9$ may optionally form, together with the nitrogen atom to which they are attached, at least one ring comprising at least one heteroatom chosen from 5-membered saturated rings and 6-membered saturated rings, wherein said at least one ring may optionally be substituted with at least one group chosen from halogen atoms, hydroxyl groups, $C_1$–$C_6$ alkyl groups, $C_1$–$C_6$ monohydroxyalkyl groups, $C_2$–$C_6$ polyhydroxyalkyl groups, nitro groups, cyano groups, cyano($C_1$–$C_6$)alkyl groups, $C_1$–$C_6$ alkoxy groups, tri($C_1$–$C_6$)alkylsilane($C_1$–$C_6$)alkyl groups, amido groups, aldehydo groups, carboxyl groups, ($C_1$–$C_6$)alkylcarbonyl groups, thio groups, $C_1$–$C_6$ thioalkyl groups, ($C_1$–$C_6$)alkylthio groups, amino groups, amino groups protected with at least one group chosen from ($C_1$–$C_6$) alkylcarbonyl groups, carbamyl groups and ($C_1$–$C_6$)alkylsulphonyl groups; and one of said $R_7$, said $R_8$ and said $R_9$ may optionally also be chosen from groups Z;

$X^-$ is chosen from monovalent anions and divalent anions;

$R_{10}$, which may be identical or different, are each chosen from $C_1$–$C_6$ alkyl groups, $C_1$–$C_6$ monohydroxyalkyl groups, $C_2$–$C_6$ polyhydroxyalkyl groups, aryl groups, benzyl groups, $C_1$–$C_6$ aminoalkyl groups, $C_1$–$C_6$ aminoalkyl group wherein said amino group is protected with at least one group chosen from ($C_1$–$C_6$)alkylcarbonyl groups, carbamyl groups and $C_1$–$C_6$ alkylsulphonyl groups, carboxy($C_1$–$C_6$) alkyl groups, cyano($C_1$–$C_6$)alkyl groups, carbamyl ($C_1$–$C_6$)alkyl groups, $C_1$–$C_6$ trifluoroalkyl groups, tri($C_1$–$C_6$)alkylsilane($C_1$–$C_6$)alkyl groups, $C_1$–$C_6$ sulphonamidoalkyl groups, ($C_1$–$C_6$)alkylcarboxy ($C_1$–$C_6$)alkyl groups, ($C_1$–$C_6$)alkylsulphinyl($C_1$–$C_6$) alkyl groups, ($C_1$–$C_6$)alkylsulphonyl($C_1$–$C_6$)alkyl groups, ($C_1$–$C_6$)alkylketo($C_1$–$C_6$)alkyl groups, N—($C_1$–$C_6$)alkylcarbamyl($C_1$–$C_6$)alkyl groups and N—($C_1$–$C_6$)alkylsulphonamido($C_1$–$C_6$)alkyl groups;

x is 0 or 1, with the proviso that:

when x=0, said linker arm B is directly bonded to at least one nitrogen atom substituted with $R_7$, $R_8$ and $R_9$;

when x=1, two of said $R_7$, $R_8$ and $R_9$ form, together with the nitrogen atom to which they are attached, at least one ring comprising at least one heteroatom chosen from 5-membered saturated rings and 6-membered saturated rings, wherein said at least one ring may optionally be substituted with at least one group chosen from halogen atoms, hydroxyl groups, $C_1$–$C_6$ alkyl groups, $C_1$–$C_6$ monohydroxyalkyl groups, $C_2$–$C_6$ polyhydroxyalkyl groups, nitro groups, cyano groups, cyano ($C_1$–$C_6$)alkyl groups, $C_1$–$C_6$ alkoxy groups, tri($C_1$–$C_6$)alkylsilane($C_1$–$C_6$)alkyl groups, amido groups, aldehydo groups, carboxyl groups, ($C_1$–$C_6$)alkylcarbonyl groups, thio groups, $C_1$–$C_6$ thioalkyl groups, ($C_1$–$C_6$)alkylthio groups, amino groups, amino groups protected with at least one group chosen ($C_1$–$C_6$)alkylcarbonyl groups, carbamyl groups and ($C_1$–$C_6$)alkylsulphonyl groups; and said linker arm B is directly bonded to at least one carbon atom of said at least one ring;

with the proviso that said monobenzenic couplers of formula (I) comprise at least one group Z; and with the further proviso that when:

said monobenzenic couplers of formula (I) comprise only one group Z, $A_1$ is chosen from groups —$NR_4R_5$ and $A_2$ is chosen from groups —$NR'_4R'_5$ wherein:

$R_4$ and $R_5$, which may be identical or different, are each chosen from hydrogen atoms, $C_1$–$C_6$ alkyl groups and $C_1$–$C_6$ hydroxyalkyl groups, and $R'_4$ and $R'_5$ are each chosen from hydrogen atoms; or $R_4$ and $R_5$ are each chosen from hydrogen atoms, and $R'_4$ and $R'_5$, which may be identical or different, are each chosen from hydrogen atoms, $C_1$–$C_6$ alkyl groups and $C_1$–$C_6$ hydroxyalkyl groups, and only one of said $R_1$, $R_2$ and $R_3$ is chosen from groups $OR_6$, wherein:

$R_6$ is chosen from groups Z, wherein:

said linker arm B is chosen from divalent $C_3$ alkyl groups monosubstituted in position 2 with a hydroxyl group, and said $R_7$, $R_8$ and $R_9$, which may be identical or different, are each chosen from $C_1$–$C_6$ alkyl groups and $C_1$–$C_6$ hydroxyalkyl groups or together with the nitrogen atom to which they are attached, form a ring chosen from morpholine rings and piperidine rings, then the other two of said $R_1$, $R_2$ and $R_3$ cannot simultaneously be chosen from hydrogen atoms.

2. A composition according to claim 1, wherein said X⁻ is chosen from halogen anions, hydroxide anions, hydrogen sulphate anions and ($C_1$–$C_6$)alkyl sulphate anions.

3. A composition according to claim 2, wherein said halogen anions are chosen from chloride, bromide, fluoride and iodide.

4. A composition according to claim 1, wherein said B is chosen from linear and branched divalent alkyl groups comprising from 1 to 14 carbon atoms.

5. A composition according to claim 1, wherein said at least one heteroatom is chosen from oxygen, sulphur and nitrogen.

6. A composition according to claim 1, wherein said two of said $R_7$, said $R_8$ and said $R_9$ form, together with the nitrogen atom to which they are attached, at least one ring comprising at least one heteroatom chosen from pyrrolidone rings, piperidine rings, piperazine rings and morpholine rings.

7. A composition according to claim 1, wherein said acid addition salts are chosen from hydrochlorides, hydrobromides, sulphates, citrates, succinates, tartrates, lactates and acetates.

8. A composition for oxidation dyeing of keratin fibres comprising, in a medium suitable for dyeing, at least one coupler chosen from:

[2-(2,4-diaminophenoxy)ethyl]diethylmethylammonium chloride;
1-[3-(2,4-diaminophenoxy)propyl]-1,4-dimethylpiperazin-1-ium chloride;
1-[(3-hydroxy-4-methylphenylcarbamoyl)methyl]-1,4-dimethylpiperazin-1-ium chloride;
1,4-bis(2-hydroxyethyl)-1-[(3-hydroxyphenylcarbamoyl)methyl]piperazin-1-ium chloride;
[3-(2,4-diaminophenoxy)propyl]triethylammonium chloride;
1-[(2,4-dihydroxyphenylcarbamoyl)methyl]-1-methylpiperidinium chloride;
[2-(2,4-dihydroxyphenyl)-2-oxoethyl]triethylammonium chloride;
1-[(3-hydroxy-4-methylphenylcarbamoyl)methyl]-1-methylpyrrolidinium chloride;
1-[(2,6-dihydroxyphenylcarbamoyl)methyl]-1-methylpyrrolidinium chloride;
[2-(4-amino-2-hydroxyphenoxy)ethyl]diethylmethylammonium chloride;
triethyl-[2-(3-hydroxy-4-methylphenylamino)ethyl]ammonium bromide;
1-[2-(3-hydroxy-4-methylphenylamino)ethyl]-1,4-dimethylpiperazin-1-ium bromide;
4-[(3-hydroxyphenylcarbamoyl)methyl]-4-methylmorpholin-4-ium chloride;
triethyl-[2-(3-hydroxy-2,4-dimethylphenylcarbamoyloxy)ethyl]ammonium chloride;
[2-(4-chloro-3-hydroxyphenylamino)ethyl]triethylammonium bromide;
1-[3-(2-amino-4-methylaminophenoxy)propyl]-1-methylpiperidinium chloride;
[2-(2,4-diaminophenoxy)ethyl]diethylmethylammonium chloride;
1-(3-trimethylammonium-2-hydroxypropyl)-1-[(3-hydroxy-4-methylphenylcarbamoyl)methyl]pyrrolidinium dichloride;
1-[2-(3-amino-4-methoxyphenylamino)ethyl]-1,4-dimethylpiperazin-1-ium bromide;
[2-(2,4-diaminophenyl)ethyl]triethylammonium chloride;
1-[(3-hydroxy-2,4-dimethylphenylcarbamoyl)methyl]-1,4-dimethylpiperazin-1-ium chloride;
N,N-bis[2-(1-methylpyrrolidinium)ethyl]benzene-1,3-diamine dichloride;
triethyl[(3-hydroxy-4-methylphenylcarbamoyl)methyl]ammonium chloride;
N,N'-bis{2-[1,4-bis(2-hydroxyethyl)piperazin-1-ium]ethyl}benzene-1,3-diamine-2-methyl dichloride;
1-[3-(2,4-diaminophenoxy)propyl]-1-methylpyrrolidinium chloride;
1-[(3-hydroxyphenylcarbamoyl)methyl]-1,4-dimethylpiperazin-1-ium chloride;
1-[3-(2,4-diaminophenoxy)propyl]-4-(3-trimethylammonium-2-hydroxypropyl)-1,4-dimethylpiperazine-1,4-diium trichloride;
[2-[4-(dimethylamino)salicylamido]ethyl]diethylmethylammonium iodide;

ethyl(2-hydroxyethyl)dimethylammonium 4-(methylamino)salicylate bromide;
3-[(4-amino-2-hydroxybenzoyl)oxy]-N-ethyl-N,N-dimethyl-1-propanaminium iodide;
3-[(4-amino-2-hydroxybenzoyl)oxy]-N,N,N-trimethyl-1-propanaminium iodide;
triethyl(2-hydroxyethyl)ammonium 4-aminosalicylate bromide;
2-[(4-amino-2-hydroxybenzoyl)oxy]-N,N-diethyl-N-methylethanaminium iodide;
2-[(4-amino-2-hydroxybenzoyl)oxy]-N-ethyl-N,N-dimethylethanaminium iodide;
ethyl(2-hydroxyethyl)dimethylammonium 4-aminosalicylate bromide;
2-[(4-amino-2-hydroxybenzoyl)oxy]-N,N,N-trimethylethanaminium iodide;

and the acid addition salts of any of the foregoing.

9. A composition according to claim 8, wherein said acid addition salts are chosen from hydrochlorides, hydrobromides, sulphates, citrates, succinates, tartrates, lactates and acetates.

10. A composition according to claim 8, wherein said monobenzenic couplers of formula (I) are chosen from:

[2-(2,4-diaminophenoxy)ethyl]diethylmethylammonium chloride;
1-[3-(2,4-diaminophenoxy)propyl]-1,4-dimethylpiperazin-1-ium chloride;
1-[(3-hydroxy-4-methylphenylcarbamoyl)methyl]-1,4-dimethylpiperazin-1-ium chloride;
1,4-bis(2-hydroxyethyl)-1-[(3-hydroxyphenylcarbamoyl)methyl]piperazin-1-ium chloride;
[3-(2,4-diaminophenoxy)propyl]triethylammonium chloride;
1-[(2,4-dihydroxyphenylcarbamoyl)methyl]-1-methylpiperidinium chloride;
[2-(2,4-dihydroxyphenyl)-2-oxoethyl]triethylammonium chloride;
1-[(3-hydroxy-4-methylphenylcarbamoyl)methyl]-1-methyl pyrrolidinium chloride;
1-[(2,6-dihydroxyphenylcarbamoyl)methyl]-1-methylpyrrolidinium chloride;
[2-(4-amino-2-hydroxyphenoxy)ethyl]diethylmethylammonium chloride;
triethyl-[2-(3-hydroxy-4-methylphenylamino)ethyl]ammonium bromide;
1-[2-(3-hydroxy-4-methylphenylamino)ethyl]-1,4-dimethylpiperazin-1-ium bromide;
4-[(3-hydroxyphenylcarbamoyl)methyl]-4-methylmorpholin-4-ium chloride;
triethyl-[2-(3-hydroxy-2,4-dimethylphenylcarbamoyloxy)ethyl]ammonium chloride;
[2-(4-chloro-3-hydroxyphenylamino)ethyl]triethylammonium bromide;
1-[3-(2-amino-4-methylaminophenoxy)propyl]-1-methylpiperidinium chloride;
[2-(2,4-diaminophenoxy)ethyl]diethylmethylammonium chloride;
1-(3-trimethylammonium-2-hydroxypropyl)-1-[(3-hydroxy-4-methylphenylcarbamoyl)methyl]pyrrolidinium dichloride;
1-[2-(3-amino-4-methoxyphenylamino)ethyl]-1,4-dimethylpiperazin-1-ium bromide;
[2-(2,4-diaminophenyl)ethyl]triethylammonium chloride;
1-[(3-hydroxy-2,4-dimethylphenylcarbamoyl)methyl]-1,4-dimethylpiperazin-1-ium chloride;
N,N-bis[2-(1-methylpyrrolidinium)ethyl]benzene-1,3-diamine dichloride;
triethyl[(3-hydroxy-4-methylphenylcarbamoyl)methyl]ammonium chloride;
N,N'-bis{2-[1,4-bis(2-hydroxyethyl)piperazin-1-ium]ethyl}benzene-1,3-diamine-2-methyl dichloride;
1-[3-(2,4-diaminophenoxy)propyl]-1-methylpyrrolidinium chloride;
1-[(3-hydroxyphenylcarbamoyl)methyl]-1,4-dimethylpiperazin-1-ium chloride;
1-[3-(2,4-diaminophenoxy)propyl]-4-(3-trimethylammonium-2-hydroxypropyl)-1,4-dimethylpiperazine-1,4-diium trichloride;

and the acid addition salts of any of the foregoing.

11. A composition according to claim 10, wherein said acid addition salts are chosen from hydrochlorides, hydrobromides, sulphates, citrates, succinates, tartrates, lactates and acetates.

12. A composition according to claim 1, wherein said at least one coupler is present in an amount ranging from 0.0005% to 12% by weight relative to the total weight of said composition.

13. A composition according to claim 12, wherein said at least one coupler is present in an amount ranging from 0.005% to 6% by weight relative to the total weight of said composition.

14. A composition according to claim 1, further comprising at least one oxidation base chosen from para-phenylenediamines, bis(phenyl)alkylenediamines, para-aminophenols, ortho-aminophenols, heterocyclic bases and the acid addition salts of any of the foregoing.

15. A composition according to claim 14, wherein said acid addition salts are chosen from hydrochlorides, hydrobromides, sulphates, citrates, succinates, tartrates, lactates and acetates.

16. A composition according to claim 14, wherein said at least one oxidation base is present in an amount ranging from 0.0005% to 12% by weight relative to the total weight of said composition.

17. A composition according to claim 16, wherein said at least one oxidation base is present in an amount ranging from 0.005% to 6% by weight relative to the total weight of said composition.

18. A composition according claim 1, further comprising at least one additional coupler chosen from meta-phenylenediamines different from said at least one coupler as defined in claim 1, meta-aminophenols different from said at least one coupler as defined in claim 1, meta-diphenols different from said at least one coupler as defined in claim 1, heterocyclic couplers different from said at least one coupler as defined in claim 1, and the acid addition salts of any of the foregoing.

19. A composition according to claim 18, wherein said acid addition salts are chosen from hydrochlorides, hydrobromides, sulphates, citrates, succinates, tartrates, lactates and acetates.

20. A composition according to claim 18, wherein said at least one additional coupler is chosen from indole derivatives different from said at least one coupler as defined in claim 1, indolene derivatives different from said at least one coupler as defined in claim 1, pyridine derivatives different from said at least one coupler as defined in claim 1, pyrazolones different from said at least one coupler as defined in claim 1 and the acid addition salts of any of the foregoing.

21. A composition according to claim 20, wherein said acid addition salts are chosen from hydrochlorides, hydrobromides, sulphates, citrates, succinates, tartrates, lactates and acetates.

22. A composition according to claim 20, wherein said at least one additional coupler is chosen from 2-methyl-5-aminophenol, 5-N-(β-hydroxyethyl)amino-2-methylphenol, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, sesamol, α-naphthol, 6-hydroxyindole, 4-hydroxyindole, 4-hydroxy-N-methylindole, 6-hydroxyindoline, 2,6-dihydroxy-4-methylpyridine, 1H-3-methylpyrazol-5-one and 1-phenyl-3-methylpyrazol-5-one and the acid addition salts of any of the foregoing.

23. A composition according to claim 22, wherein said acid addition salts are chosen from hydrochlorides, hydrobromides, sulphates, citrates, succinates, tartrates, lactates and acetates.

24. A composition according to claim 18, wherein said at least one additional coupler is present in an amount ranging from 0.0001% to 10% by weight relative to the total weight of said composition.

25. A composition according to claim 24, wherein said at least one additional coupler is present in an amount ranging from 0.005% to 5% by weight relative to the total weight of said composition.

26. A composition according to claim 1, wherein said medium suitable for dyeing is chosen from water and a mixture of water and at least one organic solvent.

27. A composition according to claim 26, wherein said at least one organic solvent is chosen from $C_1$–$C_4$ lower alkanols, glycerol, glycols, glycol ethers and aromatic alcohols.

28. A composition according to claim 1, wherein said medium suitable for dyeing is present in a proportion ranging from about 1% to about 40% by weight relative to the total weight of said composition.

29. A composition according to claim 28, wherein said medium suitable for dyeing is present in a proportion ranging from about 5% to about 30% by weight relative to the total weight of said composition.

30. A composition according to claim 1, further comprising at least one direct dye.

31. A composition according to claim 1, further comprising at least one suitable adjuvant chosen from anionic surfactants, cationic surfactants, nonionic surfactants, amphoteric surfactant, zwitterionic surfactant, anionic polymers, cationic polymers, nonionic polymers, amphoteric polymers, zwitterionic polymers, inorganic thickening agents, organic thickening agents, antioxidants, penetrating agents, sequestering agents, fragrances, buffers, dispersing agents, packaging agents, film-forming agents, ceramides, preservatives and opacifying agents.

32. A composition according to claim 1, wherein said keratin fibres are human keratin fibres.

33. A composition according to claim 32, wherein said human keratin fibres are hair.

34. A composition according to claim 1, in the form of a liquid, a cream, a gel or any other suitable form for dyeing keratin fibres.

35. A composition according to claim 1 having a pH ranging from 3 to 12.

36. A composition according to claim 35, wherein said pH ranges from 5 to 11.

37. A process for dyeing keratinous fibers comprising applying to said keratinous fibers for a sufficient time to develop a desired color at least one dyeing composition comprising at least one coupler chosen from monobenzenic couplers of formula (I) and the acid addition salts thereof:

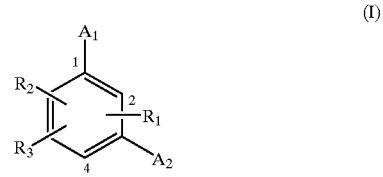

(I)

wherein:
$R_1$, $R_2$ and $R_3$, which may be identical or different, are each chosen from hydrogen atoms, halogen atoms, groups Z as defined below, groups —CO—Z, group —CO—OZ, ($C_1$–$C_6$)alkylcarbonyl groups, amino ($C_1$–$C_6$)alkylcarbonyl groups, N—Z-amino($C_1$–$C_6$) alkylcarbonyl groups, N—($C_1$–$C_6$)alkylamino($C_1$–$C_6$) alkylcarbonyl groups, N,N-di($C_1$–$C_6$)alkylamino ($C_1$–$C_6$)alkylcarbonyl groups, amino($C_1$–$C_6$) alkylcarbonyl($C_1$–$C_6$)alkyl groups, N—Z-amino ($C_1$–$C_6$)alkylcarbonyl($C_1$–$C_6$)alkyl groups, N—($C_1$–$C_6$)alkylamino($C_1$–$C_6$)alkylcarbonyl($C_1$–$C_6$) alkyl groups, N,N-di($C_1$–$C_6$)alkylamino($C_1$–$C_6$) alkylcarbonyl($C_1$–$C_6$)alkyl groups, carboxyl groups, ($C_1$–$C_6$)alkylcarboxyl groups, $C_1$–$C_6$ alkylsulphonyl groups, aminosulphonyl groups, N—Z-aminosulphonyl groups, $C_1$–$C_6$ N-alkylaminosulphonyl groups, N,N-di($C_1$–$C_6$) alkylaminosulphonyl groups, $C_1$–$C_6$ aminosulphonylalkyl groups, $C_1$–$C_6$ N—Z-aminosulphonylalkyl groups, N—($C_1$–$C_6$)alkylamihosulphonyl($C_1$–$C_6$)alkyl groups, N,N-di($C_1$–$C_6$)alkylaminosulphonyl($C_1$–$C_6$) alkyl groups, carbamyl groups, N—($C_1$–$C_6$) alkylcarbamyl groups, N,N-di($C_1$–$C_6$)alkylcarbamyl groups, carbamyl($C_1$–$C_6$)alkyl groups, N—($C_1$–$C_6$) alkylcarbamyl($C_1$–$C_6$)alkyl groups, N,N-di($C_1$–$C_6$) alkylcarbamyl($C_1$–$C_6$)alkyl groups, $C_1$–$C_6$ alkyl groups, $C_1$–$C_6$ monohydroxyalkyl groups, $C_2$–$C_6$ polyhydroxyalkyl groups, ($C_1$–$C_6$)alkoxy($C_1$–$C_6$)alkyl groups, $C_1$–$C_6$ trifluoroalkyl groups, cyano groups, groups $OR_6$, groups $R_6$ and amino groups protected with at least one group chosen from ($C_1$–$C_6$) alkylcarbonyl groups, ($C_1$–$C_6$)alkylcarboxyl groups, trifluoro($C_1$–$C_6$)alkylcarbonyl groups, amino($C_1$–$C_6$) alkylcarbonyl groups, N—Z-amino($C_1$–$C_6$) alkylcarbonyl groups, N—($C_1$–$C_6$)alkylamino($C_1$–$C_6$) alkylcarbonyl groups, N,N-di($C_1$–$C_6$)alkylamino ($C_1$–$C_6$)alkylcarbonyl groups, ($C_1$–$C_6$)alkylcarboxyl groups, carbamyl groups, N—($C_1$–$C_6$)alkylcarbamyl groups, N,N-di($C_1$–$C_6$)alkylcarbamyl groups, $C_1$–$C_6$ alkylsulphonyl groups, aminosulphonyl groups, N—Z-aminosulphonyl groups, $C_1$–$C_6$ N-alkylaminosulphonyl groups, N,N-di($C_1$–$C_6$) alkylaminosulphonyl groups, thiocarbamyl groups, formyl groups, groups —CO—Z and groups —CO—OZ; wherein:
$R_6$, which may be identical or different, are each chosen from $C_1$–$C_6$ alkyl groups, $C_1$–$C_6$ monohydroxyalkyl groups, $C_2$–$C_6$ polyhydroxyalkyl groups, groups Z as defined below, ($C_1$–$C_6$)alkoxy($C_1$–$C_6$)alkyl groups, aryl groups, benzyl groups, carboxy($C_1$–$C_6$) alkyl groups, ($C_1$–$C_6$)alkylcarboxy($C_1$–$C_6$)alkyl groups, cyano($C_1$–$C_6$)alkyl groups, carbamyl ($C_1$–$C_6$)alkyl groups, N—($C_1$–$C_6$)alkylcarbamyl ($C_1$–$C_6$)alkyl groups, N,N-di($C_1$–$C_6$)alkylcarbamyl ($C_1$–$C_6$)alkyl groups, $C_1$–$C_6$ trifluoroalkyl groups, $C_1$–$C_6$ aminosulphonylalkyl groups, $C_1$–$C_6$ N—Z-aminosulphonylalkyl groups, N—($C_1$–$C_6$) alkylaminosulphonyl($C_1$–$C_6$)alkyl groups, N,N-di($C_1$–$C_6$)alkylaminosulphonyl($C_1$–$C_6$)alkyl groups, ($C_1$–$C_6$)alkylsulphinyl($C_1$–$C_6$)alkyl groups, ($C_1$–$C_6$) alkylsulphonyl($C_1$–$C_6$)alkyl groups, ($C_1$–$C_6$) alkylcarbonyl($C_1$–$C_6$)alkyl groups, $C_1$–$C_6$ aminoalkyl groups and $C_1$–$C_6$ aminoalkyl groups wherein said amino group is substituted with one or two groups, which may be identical or different, each chosen from $C_1$–$C_6$ alkyl groups, $C_1$–$C_6$ monohydroxyalkyl groups, $C_2$–$C_6$ polyhydroxyalkyl groups, ($C_1$–$C_6$)alkylcarbonyl groups, formyl groups, trifluoro-($C_1$–$C_6$)alkylcarbonyl groups, ($C_1$–$C_6$) alkylcarboxyl groups, carbamyl groups, N—($C_1$–$C_6$) alkylcarbamyl groups, N,N-di-($C_1$–$C_6$) alkylcarbamyl groups, thiocarbamyl groups, $C_1$–$C_6$ alkylsulphonyl groups, groups Z, groups —CO—Z and groups —CO—OZ;

$A_1$ is chosen from groups —$NR_4R_5$ and hydroxyl groups, wherein $R_4$ and $R_5$ are as defined below; and $A_2$ is chosen from groups —$NR'_4R'_5$ and hydroxyl groups, wherein:

$R_4$, $R'_4$, $R_5$ and $R'_5$, which may be identical or different, are each chosen from hydrogen atoms, groups Z as defined below, $C_1$–$C_6$ alkyl groups, $C_1$–$C_6$ monohydroxyalkyl groups, $C_2$–$C_6$ polyhydroxyalkyl groups, ($C_1$–$C_6$)alkoxy($C_1$–$C_6$)alkyl groups, aryl groups, benzyl groups, cyano($C_1$–$C_6$)alkyl groups, carbamyl ($C_1$–$C_6$)alkyl groups, N—($C_1$–$C_6$)alkylcarbamyl ($C_1$–$C_6$)alkyl groups, N,N-di($C_1$–$C_6$)alkylcarbamyl ($C_1$–$C_6$)alkyl groups, thiocarbamyl($C_1$–$C_6$)alkyl groups, $C_1$–$C_6$ trifluoroalkyl groups, $C_1$–$C_6$ sulphoalkyl groups, ($C_1$–$C_6$)alkylcarboxy($C_1$–$C_6$)alkyl groups, ($C_1$–$C_6$)alkylsulphinyl($C_1$–$C_6$)alkyl groups, $C_1$–$C_6$ aminosulphonylalkyl groups, $C_1$–$C_6$ N—Z-aminosulphonylalkyl groups, N—($C_1$–$C_6$) alkylaminosulphonyl($C_1$–$C_6$)alkyl groups, N,N-di ($C_1$–$C_6$)alkylaminosulphonyl($C_1$–$C_6$)alkyl groups, ($C_1$–$C_6$)alkylcarbonyl($C_1$–$C_6$)alkyl groups, $C_1$–$C_6$ aminoalkyl groups, $C_1$–$C_6$ aminoalkyl groups wherein said amino group is substituted with one or two groups, which may be identical or different, each chosen from $C_1$–$C_6$ alkyl groups, $C_1$–$C_6$ monohydroxyalkyl groups, $C_2$–$C_6$ polyhydroxyalkyl groups, ($C_1$–$C_6$)alkylcarbonyl groups, carbamyl groups, N—($C_1$–$C_6$)alkylcarbamyl groups, N,N-di($C_1$–$C_6$) alkylcarbamyl groups, $C_1$–$C_6$ alkylsulphonyl groups, formyl groups, trifluoro($C_1$–$C_6$) alkylcarbonyl groups, ($C_1$–$C_6$)alkylcarboxyl groups, thiocarbamyl groups, groups Z, groups —CO—Z and groups —CO—OZ, wherein:

one of said $R_4$, $R'_4$, $R_5$ and $R'_5$, which may be identical or different, may optionally also be chosen from ($C_1$–$C_6$)alkylcarboxyl groups, ($C_1$–$C_6$) alkylcarbonyl groups, formyl groups, trifluoro ($C_1$–$C_6$)alkylcarbonyl groups, amino($C_1$–$C_6$) alkylcarbonyl groups, N—Z-amino($C_1$–$C_6$) alkylamino carbonyl groups, N—($C_1$–$C_6$)alkylamino ($C_1$–$C_6$)alkylcarbonyl groups, N,N-di($C_1$–$C_6$) alkylamino($C_1$–$C_6$)alkylcarbonyl groups, carbamyl groups, N—($C_1$–$C_6$)alkylcarbamyl groups, N,N-di($C_1$–$C_6$)alkylcarbamyl groups, thiocarbamyl groups, aminosulphonyl groups, N—Z-aminosulphonyl groups, N—($C_1$–$C_6$) alkylaminosulphonyl groups, N,N-di($C_1$–$C_6$) alkylaminosulphonyl groups, ($C_1$–$C_6$) alkylsulphonyl groups, groups —CO—Z and groups —CO—OZ;

groups Z, which may be identical or different, are each chosen from groups of formula (II):

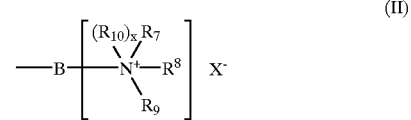

(II)

wherein:

B is a linker arm chosen from linear and branched divalent alkyl groups, which are optionally interrupted by at least one heteroatom and which are optionally substituted with at least one group chosen from hydroxyl groups and $C_1$–$C_6$ alkoxy groups;

$R_7$, $R_8$ and $R_9$, which may be identical or different, are each chosen from $C_1$–$C_6$ alkyl groups, $C_1$–$C_6$ monohydroxyalkyl groups, $C_2$–$C_6$ polyhydroxyalkyl groups, ($C_1$–$C_6$)alkoxy($C_1$–$C_6$)alkyl groups, cyano ($C_1$–$C_6$)alkyl groups, aryl groups, benzyl groups, carbamyl($C_1$–$C_6$)alkyl groups, N—($C_1$–$C_6$) alkylcarbamyl($C_1$–$C_6$)alkyl groups, tri($C_1$–$C_6$) alkylsilane($C_1$–$C_6$)alkyl groups and $C_1$–$C_6$ aminoalkyl groups wherein said amino group is protected with at least one group chosen from ($C_1$–$C_6$)alkylcarbonyl groups, carbamyl groups and ($C_1$–$C_6$)alkylsulphonyl groups, wherein:

two of said $R_7$, said $R_8$ and said $R_9$ may optionally form, together with the nitrogen atom to which they are attached, at least one ring comprising at least one heteroatom chosen from 5-membered saturated rings and 6-membered saturated rings, wherein said at least one ring may optionally be substituted with at least one group chosen from halogen atoms, hydroxyl groups, $C_1$–$C_6$ alkyl groups, $C_1$–$C_6$ monohydroxyalkyl groups, $C_2$–$C_6$ polyhydroxyalkyl groups, nitro groups, cyano groups, cyano($C_1$–$C_6$)alkyl groups, $C_1$–$C_6$ alkoxy groups, tri($C_1$–$C_6$)alkylsilane($C_1$–$C_6$)alkyl groups, amido groups, aldehydo groups, carboxyl groups, ($C_1$–$C_6$)alkylcarbonyl groups, thio groups, $C_1$–$C_6$ thioalkyl groups, ($C_1$–$C_6$)alkylthio groups, amino groups, amino groups protected with at least one group chosen from ($C_1$–$C_6$) alkylcarbonyl groups, carbamyl groups and ($C_1$–$C_6$)alkylsulphonyl groups; and one of said $R_7$, said $R_8$ and said $R_9$ may optionally also be chosen from groups Z;

$X^-$ is chosen from monovalent anions and divalent anions;

$R_{10}$, which may be identical or different, are each chosen from $C_1$–$C_6$ alkyl groups, $C_1$–$C_6$ monohydroxyalkyl groups, $C_2$–$C_6$ polyhydroxyalkyl groups, aryl groups, benzyl groups, $C_1$–$C_6$ aminoalkyl groups, $C_1$–$C_6$ aminoalkyl group wherein said amino group is protected with at least one group chosen from ($C_1$–$C_6$)alkylcarbonyl groups, carbamyl groups and $C_1$–$C_6$ alkylsulphonyl groups, carboxy($C_1$–$C_6$) alkyl groups, cyano($C_1$–$C_6$)alkyl groups, carbamyl ($C_1$–$C_6$)alkyl groups, $C_1$–$C_6$ trifluoroalkyl groups, tri($C_1$–$C_6$)alkylsilane($C_1$–$C_6$)alkyl groups, $C_1$–$C_6$ sulphonamidoalkyl groups, ($C_1$–$C_6$)alkylcarboxy ($C_1$–$C_6$)alkyl groups, ($C_1$–$C_6$)alkylsulphinyl($C_1$–$C_6$) alkyl groups, ($C_{C6}$)alkylsulphonyl($C_1$–$C_6$)alkyl groups, $(C_1-C_6)$alkylketo$(C_1-C_6)$alkyl groups, N—$(C_1-C_6)$alkylcarbamyl$(C_1-C_6)$alkyl groups and N—$(C_1-C_6)$alkylsulphonamido$(C_1-C_6)$alkyl groups;

x is 0 or 1, with the proviso that:

when x=0, said linker arm B is directly bonded to at least one nitrogen atom substituted with $R_7$, $R_8$ and $R_9$;

when x=1, two of said $R_7$, $R_8$ and $R_9$ form, together with the nitrogen atom to which they are attached, at least one ring comprising at least one heteroatom chosen from 5-membered saturated rings and 6-membered saturated rings, wherein said at least one ring may optionally be substituted with at least one group chosen from halogen atoms, hydroxyl groups, $C_1-C_6$ alkyl groups, $C_1-C_6$ monohydroxyalkyl groups, $C_2-C_6$ polyhydroxyalkyl groups, nitro groups, cyano groups, cyano $(C_1-C_6)$alkyl groups, $C_1-C_6$ alkoxy groups, tri$(C_1-C_6)$alkylsilane$(C_1-C_6)$alkyl groups, amido groups, aldehydo groups, carboxyl groups, $(C_1-C_6)$alkylcarbonyl groups, thio groups, $C_1-C_6$ thioalkyl groups, $(C_1-C_6)$alkylthio groups, amino groups, amino groups protected with at least one group chosen from $(C_1-C_6)$alkylcarbonyl groups, carbamyl groups and $(C_1-C_6)$alkylsulphonyl groups; and said linker arm B is directly bonded to at least one carbon atom of said at least one ring;

with the proviso that said monobenzenic couplers of formula (I) comprise at least one group Z; and with the further proviso that when:

said monobenzenic couplers of formula (I) comprise only one group Z, $A_1$ is chosen from groups —$NR_4R_5$ and A2 is chosen from groups —$NR'_4R'_5$ wherein:

$R_4$ and $R_5$, which may be identical or different, are each chosen from hydrogen atoms, $C_1-C_6$ alkyl groups and $C_1-C_6$ hydroxyalkyl groups, and $R'_4$ and $R'_5$ are each chosen from hydrogen atoms; or $R_4$ and $R_5$ are each chosen from hydrogen atoms, and $R'_4$ and $R'_5$, which may be identical or different, are each chosen from hydrogen atoms, $C_1-C_6$ alkyl groups and $C_1-C_6$ hydroxyalkyl groups, and only one of said $R_1$, $R_2$ and $R_3$ is chosen from groups $OR_6$, wherein:

$R_6$ is chosen from groups Z, wherein:

said linker arm B is chosen from divalent $C_3$ alkyl groups monosubstituted in position 2 with a hydroxyl group, and said $R_7$, $R_8$ and $R_9$, which may be identical or different, are each chosen from $C_1-C_6$ alkyl groups and $C_1-C_6$ hydroxyalkyl groups or together with the nitrogen atom to which they are attached, form a ring chosen from morpholine rings and piperidine rings, then the other two of said $R_1$, $R_2$ and $R_3$ cannot simultaneously be chosen from hydrogen atoms, in a medium suitable for dyeing.

38. A process according to claim 37, wherein said desired colour is developed at acidic, neutral or alkaline pH using at least one oxidizing agent.

39. A process according to claim 38, wherein said at least one oxidizing agent is added to said at least one dyeing composition immediately prior to use.

40. A process according to claim 38, wherein said at least one oxidizing agent is comprised in at least one oxidizing composition.

41. A process according to claim 40, wherein said at least one oxidizing composition is applied to said keratinous fibres simultaneously with said at least one dyeing composition.

42. A process according to claim 40, wherein said at least one oxidizing composition is applied to said keratinous fibres sequentially with said at least one dyeing composition.

43. A process according to claim 27, wherein said keratinous fibres are human keratin fibres.

44. A process according to claim 43, wherein said human keratin fibres are hair.

45. A process according to claim 37, wherein said sufficient time to develop a desired color ranges from about 3 minutes to about 50 minutes.

46. A process according to claim 45, wherein said sufficient time to develop a desired color ranges from about 5 minutes to about 30 minutes.

47. A process according to claim 37, further comprising rinsing said keratinous fibres.

48. A process according to claim 47, further comprising washing said keratinous fibres with shampoo.

49. A process according to claim 48, further comprising rinsing said keratinous fibres.

50. A process according to claim 38, wherein said at least one oxidizing agent is chosen from hydrogen peroxide, urea peroxide, alkali metal bromates, persalts and enzymes.

51. A process according to claim 50, wherein said persalts are choen from perborates and persulphates.

52. A process according to claim 50, wherein said enzymes are chosen from peroxidases and 2-electron oxidoreductases.

53. A process according to claim 50, wherein said at least one oxidizing agent is chosen from hydrogen peroxide.

54. A multi-compartment dyeing device or kit comprising:
(a) a first compartment comprising a first composition
(b) a second compartment comprising a second composition
wherein said first composition comprises at least one dyeing composition comprising at least one coupler chosen from monobenzenic couplers of formula (I) and the acid addition salts thereof:

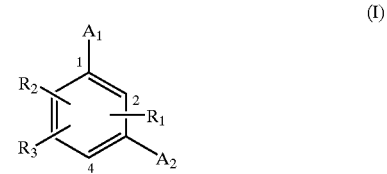

(I)

wherein:

$R_1$, $R_2$ and $R_3$, which may be identical or different, are each chosen from hydrogen atoms, halogen atoms, groups Z as defined below, groups —CO—Z, group —CO—OZ, $(C_1-C_6)$alkylcarbonyl groups, amino $(C_1-C_6)$alkylcarbonyl groups, N—Z-amino$(C_1-C_6)$alkylcarbonyl groups, N—$(C_1-C_6)$alkylamino$(C_1-C_6)$alkylcarbonyl groups, N,N-di$(C_1-C_6)$alkylamino$(C_1-C_6)$alkylcarbonyl groups, amino$(C_1-C_6)$alkylcarbonyl$(C_1-C_6)$alkyl groups, N—Z-amino$(C_1-C_6)$alkylcarbonyl$(C_1-C_6)$alkyl groups, N—$(C_1-C_6)$alkylamino$(C_1-C_6)$alkylcarbonyl$(C_1-C_6)$alkyl groups, N,N-di$(C_1-C_6)$alkylamino$(C_1-C_6)$alkylcarbonyl$(C_1-C_6)$alkyl groups, carboxyl groups, $(C_1-C_6)$alkylcarboxyl groups, $C_1-C_6$ alkylsulphonyl groups, aminosulphonyl groups, N—Z-aminosulphonyl groups, $C_1-C_6$ N-alkylaminosulphonyl groups, N,N-di$(C_1-C_6)$ alkylaminosulphonyl groups, $C_1$–$C_6$ aminosulphonylalkyl groups, $C_1$–$C_6$ N—Z-aminosulphonylalkyl groups, N—($C_1$–$C_6$)alkylaminosulphonyl($C_1$–$C_6$)alkyl groups, N,N-di($C_1$–$C_6$)alkylaminosulphonyl($C_1$–$C_6$)alkyl groups, carbamyl groups, N—($C_1$–$C_6$)alkylcarbamyl groups, N,N-di($C_1$–$C_6$)alkylcarbamyl groups, carbamyl($C_1$–$C_6$)alkyl groups, N—($C_1$–$C_6$)alkylcarbamyl($C_1$–$C_6$)alkyl groups, N,N-di($C_1$–$C_6$)alkylcarbamyl($C_1$–$C_6$)alkyl groups, $C_1$–$C_6$ alkyl groups, $C_1$–$C_6$ monohydroxyalkyl groups, $C_2$–$C_6$ polyhydroxyalkyl groups, ($C_1$–$C_6$)alkoxy($C_1$–$C_6$)alkyl groups, $C_1$–$C_6$ trifluoroalkyl groups, cyano groups, groups $OR_6$, groups $R_6$ and amino groups protected with at least one group chosen from ($C_1$–$C_6$)alkylcarbonyl groups, ($C_1$–$C_6$)alkylcarboxyl groups, trifluoro($C_1$–$C_6$)alkylcarbonyl groups, amino($C_1$–$C_6$)alkylcarbonyl groups, N—Z-amino($C_1$–$C_6$)alkylcarbonyl groups, N—($C_1$–$C_6$)alkylamino($C_1$–$C_6$)alkylcarbonyl groups, N,N-di($C_1$–$C_6$)alkylamino($C_1$–$C_6$)alkylcarbonyl groups, ($C_1$–$C_6$)alkylcarboxyl groups, carbamyl groups, N—($C_1$–$C_6$)alkylcarbamyl groups, N,N-di($C_1$–$C_6$)alkylcarbamyl groups, $C_1$–$C_6$ alkylsulphonyl groups, aminosulphonyl groups, N—Z-aminosulphonyl groups, $C_1$–$C_6$ N-alkylaminosulphonyl groups, N,N-di($C_1$–$C_6$) alkylaminosulphonyl groups, thiocarbamyl groups, formyl groups, groups —CO—Z and groups —CO—OZ; wherein:

$R_6$, which may be identical or different, are each chosen from $C_1$–$C_6$ alkyl groups, $C_1$–$C_6$ monohydroxyalkyl groups, $C_2$–$C_6$ polyhydroxyalkyl groups, groups Z as defined below, ($C_1$–$C_6$)alkoxy($C_1$–$C_6$)alkyl groups, aryl groups, benzyl groups, carboxy($C_1$–$C_6$)alkyl groups, ($C_1$–$C_6$)alkylcarboxy($C_1$–$C_6$)alkyl groups, cyano($C_1$–$C_6$)alkyl groups, carbamyl($C_1$–$C_6$)alkyl groups, N—($C_1$–$C_6$)alkylcarbamyl($C_1$–$C_6$)alkyl groups, N,N-di($C_1$–$C_6$)alkylcarbamyl($C_1$–$C_6$)alkyl groups, $C_1$–$C_6$ trifluoroalkyl groups, $C_1$–$C_6$ aminosulphonylalkyl groups, $C_1$–$C_6$ N—Z-aminosulphonylalkyl groups, N—($C_1$–$C_6$)alkylaminosulphonyl($C_1$–$C_6$)alkyl groups, N,N-di($C_1$–$C_6$)alkylaminosulphonyl($C_1$–$C_6$)alkyl groups, ($C_1$–$C_6$)alkylsulphinyl($C_1$–$C_6$)alkyl groups, ($C_1$–$C_6$)alkylsulphonyl($C_1$–$C_6$)alkyl groups, ($C_1$–$C_6$)alkylcarbonyl($C_1$–$C_6$)alkyl groups, $C_1$–$C_6$ aminoalkyl groups and $C_1$–$C_6$ aminoalkyl groups wherein said amino group is substituted with one or two groups, which may be identical or different, each chosen from $C_1$–$C_6$ alkyl groups, $C_1$–$C_6$ monohydroxyalkyl groups, $C_2$–$C_6$ polyhydroxyalkyl groups, ($C_1$–$C_6$)alkylcarbonyl groups, formyl groups, trifluoro-($C_1$–$C_6$)alkylcarbonyl groups, ($C_1$–$C_6$)alkylcarboxyl groups, carbamyl groups, N—($C_1$–$C_6$)alkylcarbamyl groups, N,N-di-($C_1$–$C_6$)alkylcarbamyl groups, thiocarbamyl groups, $C_1$–$C_6$ alkylsulphonyl groups, groups Z, groups —CO—Z and groups —CO—OZ;

$A_1$ is chosen from groups —$NR_4R_5$ and hydroxyl groups, wherein $R_4$ and $R_5$ are as defined below; and $A_2$ is chosen from groups —$NR'_4R'_5$ and hydroxyl groups, wherein:

$R_4$, $R'_4$, $R_5$ and $R'_5$, which may be identical or different, are each chosen from hydrogen atoms, groups Z as defined below, $C_1$–$C_6$ alkyl groups, $C_1$–$C_6$ monohydroxyalkyl groups, $C_2$–$C_6$ polyhydroxyalkyl groups, ($C_1$–$C_6$)alkoxy($C_1$–$C_6$)alkyl groups, aryl groups, benzyl groups, cyano($C_1$–$C_6$)alkyl groups, carbamyl ($C_1$–$C_6$)alkyl groups, N—($C_1$–$C_6$)alkylcarbamyl ($C_1$–$C_6$)alkyl groups, N,N-di($C_1$–$C_6$)alkylcarbamyl ($C_1$–$C_6$)alkyl groups, thiocarbamyl($C_1$–$C_6$)alkyl groups, $C_1$–$C_6$ trifluoroalkyl groups, $C_1$–$C_6$ sulphoalkyl groups, ($C_1$–$C_6$)alkylcarboxy($C_1$–$C_6$)alkyl groups, ($C_1$–$C_6$)alkylsulphinyl($C_1$–$C_6$)alkyl groups, $C_1$–$C_6$ aminosulphonylalkyl groups, $C_1$–$C_6$ N—Z-aminosulphonylalkyl groups, N—($C_1$–$C_6$)alkylaminosulphonyl($C_1$–$C_6$)alkyl groups, N,N-di($C_1$–$C_6$)alkylaminosulphonyl($C_1$–$C_6$)alkyl groups, ($C_1$–$C_6$)alkylcarbonyl($C_1$–$C_6$)alkyl groups, $C_1$–$C_6$ aminoalkyl groups, $C_1$–$C_6$ aminoalkyl groups wherein said amino group is substituted with one or two groups, which may be identical or different, each chosen from $C_1$–$C_6$ alkyl groups, $C_1$–$C_6$ monohydroxyalkyl groups, $C_2$–$C_6$ polyhydroxyalkyl groups, ($C_1$–$C_6$)alkylcarbonyl groups, carbamyl groups, N—($C_1$–$C_6$)alkylcarbamyl groups, N,N-di($C_1$–$C_6$)alkylcarbamyl groups, $C_1$–$C_6$ alkylsulphonyl groups, formyl groups, trifluoro($C_1$–$C_6$)alkylcarbonyl groups, ($C_1$–$C_6$)alkylcarboxyl groups, thiocarbamyl groups, groups Z, groups —CO—Z and groups —CO—OZ, wherein:

one of said $R_4$, $R'_4$, $R_5$ and $R'_5$, which may be identical or different, may optionally also be chosen from ($C_1$–$C_6$)alkylcarboxyl groups, ($C_1$–$C_6$) alkylcarbonyl groups, formyl groups, trifluoro ($C_1$–$C_6$)alkylcarbonyl groups, amino($C_1$–$C_6$) alkylcarbonyl groups, N—Z-amino($C_1$–$C_6$) alkylcarbonyl groups, N—($C_1$–$C_6$)alkylamino ($C_1$–$C_6$)alkylcarbonyl groups, N,N-di($C_1$–$C_6$) alkylamino($C_1$–$C_6$)alkylcarbonyl groups, carbamyl groups, N—($C_1$–$C_6$)alkylcarbamyl groups, N,N-di($C_1$–$C_6$)alkylcarbamyl groups, thiocarbamyl groups, aminosulphonyl groups, N—Z-aminosulphonyl groups, N—($C_1$–$C_6$) alkylaminosulphonyl groups, N,N-di($C_1$–$C_6$) alkylaminosulphonyl groups, ($C_1$–$C_6$) alkylsulphonyl groups, groups —CO—Z and groups —CO—OZ;

groups Z, which may be identical or different, are each chosen from groups of formula (II):

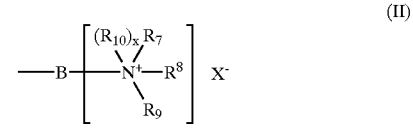

wherein:

B is a linker arm chosen from linear and branched divalent alkyl groups, which are optionally interrupted by at least one heteroatom and which are optionally substituted with at least one group chosen from hydroxyl groups and $C_1$–$C_6$ alkoxy groups;

$R_7$, $R_8$ and $R_9$, which may be identical or different, are each chosen from $C_1$–$C_6$ alkyl groups, $C_1$–$C_6$ monohydroxyalkyl groups, $C_2$–$C_6$ polyhydroxyalkyl groups, ($C_1$–$C_6$)alkoxy($C_1$–$C_6$)alkyl groups, cyano ($C_1$–$C_8$)alkyl groups, aryl groups, benzyl groups, carbamyl($C_1$–$C_6$)alkyl groups, N—($C_1$–$C_6$) alkylcarbamyl($C_1$–$C_6$)alkyl groups, tri($C_1$–$C_6$) alkylsilane($C_1$–$C_6$)alkyl groups and $C_1$–$C_6$ aminoalkyl groups wherein said amino group is protected with at least one group chosen from ($C_1$–$C_6$)alkylcarbonyl groups, carbamyl groups and ($C_1$–$C_6$)alkylsulphonyl groups, wherein:

two of said $R_7$, said $R_8$ and said $R_9$ may optionally form, together with the nitrogen atom to which they are attached, at least one ring comprising at least one heteroatom chosen from 5-membered saturated rings and 6-membered saturated rings, wherein said at least one ring may optionally be substituted with at least one group chosen from halogen atoms, hydroxyl groups, $C_1$–$C_6$ alkyl groups, $C_1$–$C_6$ monohydroxyalkyl groups, $C_2$–$C_6$ polyhydroxyalkyl groups, nitro groups, cyano groups, cyano($C_1$–$C_6$)alkyl groups, $C_1$–$C_6$ alkoxy groups, tri($C_1$–$C_6$)alkylsilane($C_1$–$C_6$)alkyl groups, amido groups, aldehydo groups, carboxyl groups, ($C_1$–$C_6$)alkylcarbonyl groups, thio groups, $C_1$–$C_6$ thioalkyl groups, ($C_1$–$C_6$)alkylthio groups, amino groups, amino groups protected with at least one group chosen from ($C_1$–$C_6$) alkylcarbonyl groups, carbamyl groups and ($C_1$–$C_6$)alkylsulphonyl groups; and one of said $R_7$, said $R_8$ and said $R_9$ may optionally also be chosen from groups Z;

$X^-$ is chosen from monovalent anions and divalent anions;

$R_{10}$, which may be identical or different, are each chosen from $C_1$–$C_6$ alkyl groups, $C_1$–$C_6$ monohydroxyalkyl groups, $C_2$–$C_6$ polyhydroxyalkyl groups, aryl groups, benzyl groups, $C_1$–$C_6$ aminoalkyl groups, $C_1$–$C_6$ aminoalkyl group wherein said amino group is protected with at least one group chosen from ($C_1$–$C_6$)alkylcarbonyl groups, carbamyl groups and $C_1$–$C_6$ alkylsulphonyl groups, carboxy($C_1$–$C_6$) alkyl groups, cyano($C_1$–$C_6$)alkyl groups, carbamyl ($C_1$–$C_6$)alkyl groups, $C_1$–$C_6$ trifluoroalkyl groups, tri($C_1$–$C_6$)alkylsilane($C_1C_6$)alkyl groups, $C_1$–$C_6$ sulphonamidoalkyl groups, ($C_1$–$C_6$)alkylcarboxy($C_1$–$C_6$)alkyl groups, ($C_1$–$C_6$)alkylsulphinyl($C_1$–$C_6$) alkyl groups, ($C_1$–$C_6$)alkylsulphonyl($C_1$–$C_6$)alkyl groups, ($C_1$–$C_6$)alkylketo($C_1$–$C_6$)alkyl groups, N—($C_1$–$C_6$)alkylcarbamyl($C_1$–$C_6$)alkyl groups and N—($C_1$–$C_6$)alkylsulphonamido($C_1$–$C_6$)alkyl groups;

x is 0 or 1, with the proviso that:
when x=0, said linker arm B is directly bonded to at least one nitrogen atom substituted with $R_7$, $R_8$ and $R_9$;
when x=1, two of said $R_7$, $R_8$ and $R_9$ form, together with the nitrogen atom to which they are attached, at least one ring comprising at least one heteroatom chosen from 5-membered saturated rings and 6-membered saturated rings, wherein said at least one ring may optionally be substituted with at least one group chosen from halogen atoms, hydroxyl groups, $C_1$–$C_6$ alkyl groups, $C_1$–$C_6$ monohydroxyalkyl groups, $C_2$–$C_6$ polyhydroxyalkyl groups, nitro groups, cyano groups, cyano ($C_1$–$C_6$)alkyl groups, $C_1$–$C_6$ alkoxy groups, tri ($C_1$–$C_6$)alkylsilane($C_1$–$C_6$)alkyl groups, amido groups, aldehydo groups, carboxyl groups, ($C_1$–$C_6$)alkylcarbonyl groups, thio groups, $C_1$–$C_6$ thioalkyl groups, ($C_1$–$C_6$)alkylthio groups, amino groups, amino groups protected with at least one group chosen from ($C_1$–$C_6$)alkylcarbonyl groups, carbamyl groups and ($C_1$–$C_6$)alkylsulphonyl groups; and said linker arm B is directly bonded to at least one carbon atom of said at least one ring;

with the proviso that said monobenzenic couplers of formula (I) comprise at least one group Z; and with the further proviso that when:

said monobenzenic couplers of formula (I) comprise only one group Z, $A_1$ is chosen from groups —$NR_4R_5$ and A2 is chosen from groups —$NR'_4R'_5$ wherein:
$R_4$ and $R_5$, which may be identical or different, are each chosen from hydrogen atoms, $C_1$–$C_6$ alkyl groups and $C_1$–$C_6$ hydroxyalkyl groups, and $R'_4$ and $R'_5$ are each chosen from hydrogen atoms; or
$R_4$ and $R_5$ are each chosen from hydrogen atoms, and $R'_4$ and $R'_5$, which may be identical or different, are each chosen from hydrogen atoms, $C_1$–$C_6$ alkyl groups and $C_1$–$C_6$ hydroxyalkyl groups, and only one of said $R_1$, $R_2$ and $R_3$ is chosen from groups $OR_6$, wherein:
$R_6$ is chosen from groups Z, wherein:
said linker arm B is chosen from divalent $C_3$ alkyl groups monosubstituted in position 2 with a hydroxyl group, and
said $R_7$, $R_8$ and $R_9$, which may be identical or different, are each chosen from $C_1$–$C_6$ alkyl groups and $C_1$–$C_6$ hydroxyalkyl groups or together with the nitrogen atom to which they are attached, form a ring chosen from morpholine rings and piperidine rings, then the other two of said $R_1$, $R_2$ and $R_3$ cannot simultaneously be chosen from hydrogen atoms, and wherein said second composition comprises at least one oxidizing composition.

55. A compound of formula (I') or an acid addition salt thereof:

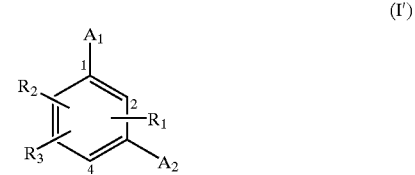

(I')

wherein:
$R_1$, $R_2$ and $R_3$, which may be identical or different, are each chosen from hydrogen atoms, halogen atoms, groups Z as defined below, groups —CO—Z, group —CO—OZ, ($C_1$–$C_6$)alkylcarbonyl groups, amino ($C_1$–$C_6$)alkylcarbonyl groups, N—Z-amino($C_1$–$C_6$) alkylcarbonyl groups, N—($C_1$–$C_6$)alkylamino($C_1$–$C_6$) alkylcarbonyl groups, N,N-di($C_1$–$C_6$)alkylamino ($C_1$–$C_6$)alkylcarbonyl groups, amino($C_1$–$C_6$) alkylcarbonyl($C_1$–$C_6$)alkyl groups, N—Z-amino ($C_1$–$C_6$)alkylcarbonyl($C_1$–$C_6$)alkyl groups, N—($C_1$–$C_6$)alkylamino($C_1$–$C_6$)alkylcarbonyl($C_1$–$C_6$) alkyl groups, N,N-di($C_1$–$C_6$)alkylamino($C_1$–$C_6$) alkylcarbonyl($C_1$–$C_6$)alkyl groups, carboxyl groups, ($C_1$–$C_6$)alkylcarboxyl groups, $C_1$–$C_6$ alkylsulphonyl groups, aminosulphonyl groups, N—Z-aminosulphonyl groups, $C_1$–$C_6$ N-alkylaminosulphonyl groups, N,N-di($C_1$–$C_6$) alkylaminosulphonyl groups, $C_1$–$C_6$ aminosulphonylalkyl groups, $C_1$–$C_6$ N—Z-aminosulphonylalkyl groups, N—($C_1$–$C_6$)alkylaminosulphonyl($C_1$–$C_6$)alkyl groups, N,N-di($C_1$–$C_6$)alkylaminosulphonyl($C_1$–$C_6$) alkyl groups, carbamyl groups, N—($C_1$–$C_6$) alkylcarbamyl groups, N,N-di($C_1$–$C_6$)alkylcarbamyl groups, carbamyl($C_1$–$C_6$)alkyl groups, N—($C_1$–$C_6$) alkylcarbamyl($C_1$–$C_6$)alkyl groups, N,N-di($C_1$–$C_6$) alkylcarbamyl($C_1$–$C_6$)alkyl groups, $C_1$–$C_6$ alkyl groups, $C_1$–$C_6$ monohydroxyalkyl groups, $C_2$–$C_6$ polyhydroxyalkyl groups, $(C_1-C_6)$alkoxy$(C_1-C_6)$alkyl groups, $C_1-C_6$ trifluoroalkyl groups, cyano groups, groups $OR_6$, groups $R_6$ and amino groups protected with at least one group chosen from $(C_1-C_6)$ alkylcarbonyl groups, $(C_1-C_6)$alkylcarboxyl groups, trifluoro$(C_1-C_6)$alkylcarbonyl groups, amino$(C_1-C_6)$ alkylcarbonyl groups, N—Z-amino$(C_1-C_6)$ alkylcarbonyl groups, N—$(C_1-C_6)$alkylamino$(C_1-C_6)$ alkylcarbonyl groups, N,N-di$(C_1-C_6)$alkylamino $(C_1-C_6)$alkylcarbonyl groups, $(C_1-C_6)$alkylcarboxyl groups, carbamyl groups, N—$(C_1-C_6)$alkylcarbamyl groups, N,N-di$(C_1-C_6)$alkylcarbamyl groups, $C_1-C_6$ alkylsulphonyl groups, aminosulphonyl groups, N—Z-aminosulphonyl groups, $C_1-C_6$ N-alkylaminosulphonyl groups, N,N-di$(C_1-C_6)$ alkylaminosulphonyl groups, thiocarbamyl groups, formyl groups, groups —CO—Z and groups —CO—OZ; wherein:

$R_6$, which may be identical or different, are each chosen from $C_1-C_6$ alkyl groups, $C_1-C_6$ monohydroxyalkyl groups, $C_2-C_6$ polyhydroxyalkyl groups, groups Z as defined below, $(C_1-C_6)$alkoxy$(C_1-C_6)$alkyl groups, aryl groups, benzyl groups, carboxy$(C_1-C_6)$ alkyl groups, $(C_1-C_6)$alkylcarboxy$(C_1-C_6)$alkyl groups, cyano$(C_1-C_6)$alkyl groups, carbamyl $(C_1-C_6)$alkyl groups, N—$(C_1-C_6)$alkylcarbamyl $(C_1-C_6)$alkyl groups, N,N-di$(C_1-C_6)$alkylcarbamyl $(C_1-C_6)$alkyl groups, $C_1-C_6$ trifluoroalkyl groups, $C_1-C_6$ aminosulphonylalkyl groups, $C_1-C_6$ N—Z-aminosulphonylalkyl groups, N—$(C_1-C_6)$ alkylaminosulphonyl$(C_1-C_6)$alkyl groups, N,N-di $(C_1-C_6)$alkylaminosulphonyl$(C_1-C_6)$alkyl groups, $(C_1-C_6)$alkylsulphinyl$(C_1-C_6)$alkyl groups, $(C_1-C_6)$ alkylsulphonyl$(C_1-C_6)$alkyl groups, $(C_1-C_6)$ alkylcarbonyl$(C_1-C_6)$alkyl groups, $C_1-C_6$ aminoalkyl groups and $C_1-C_6$ aminoalkyl groups wherein said amino group is substituted with one or two groups, which may be identical or different, each chosen from $C_1-C_6$ alkyl groups, $C_1-C_6$ monohydroxyalkyl groups, $C_2-C_6$ polyhydroxyalkyl groups, $(C_1-C_6)$alkylcarbonyl groups, formyl groups, trifluoro-$(C_1-C_6)$alkylcarbonyl groups, $(C_1-C_6)$ alkylcarboxyl groups, carbamyl groups, N—$(C_1-C_6)$ alkylcarbamyl groups, N,N-di-$(C_1-C_6)$ alkylcarbamyl groups, thiocrbamyl groups, $C_1-C_6$ alkylsulphonyl groups, groups Z, groups —CO—Z and groups —CO—OZ;

$A_1$ is chosen from groups —$NR_4R_5$ and hydroxyl groups, wherein $R_4$ and $R_5$ are as defined below; and $A_2$ is chosen from groups —$NR'_4R'_5$ and hydroxyl groups, wherein:

$R_4$, $R'_4$, $R_5$ and $R'_5$, which may be identical or different, are each chosen from hydrogen atoms, groups Z as defined below, $C_1-C_6$ alkyl groups, $C_1-C_6$ monohydroxyalkyl groups, $C_2-C_6$ polyhydroxyalkyl groups, $(C_1-C_6)$alkoxy$(C_1-C_6)$alkyl groups, aryl groups, benzyl groups, cyano$(C_1-C_6)$alkyl groups, carbamyl $(C_1-C_6)$alkyl groups, N—$(C_1-C_6)$alkylcarbamyl $(C_1-C_6)$alkyl groups, N,N-di$(C_1-C_6)$alkylcarbamyl $(C_1-C_6)$alkyl groups, thiocarbamyl$(C_1-C_6)$alkyl groups, $C_1-C_6$ trifluoroalkyl groups, $C_1-C_6$ sulphoalkyl groups, $(C_1-C_6)$alkylcarboxy$(C_1-C_6)$alkyl groups, $(C_1-C_6)$alkylsulphinyl$(C_1-C_6)$alkyl groups, $C_1-C_6$ aminosulphonylalkyl groups, $C_1-C_6$ N—Z-aminosulphonylalkyl groups, N—$(C_1-C_6)$ alkylaminosulphonyl$(C_1-C_6)$alkyl groups, N,N-di $(C_1-C_6)$alkylaminosulphonyl$(C_1-C_6)$alkyl groups, $(C_1-C_6)$alkylcarbonyl$(C_1-C_6)$alkyl groups, $C_1-C_6$ aminoalkyl groups, $C_1-C_6$ aminoalkyl groups wherein said amino group is substituted with one or two groups, which may be identical or different, each chosen from $C_1-C_6$ alkyl groups, $C_1-C_6$ monohydroxyalkyl groups, $C_2-C_6$ polyhydroxyalkyl groups, $(C_1-C_6)$alkylcarbonyl groups, carbamyl groups, N—$(C_1-C_6)$alkylcarbamyl groups, N,N-di$(C_1-C_6)$ alkylcarbamyl groups, $C_1-C_6$ alkylsulphonyl groups, formyl groups, trifluoro$(C_1-C_6)$ alkylcarbonyl groups, $(C_1-C_6)$alkylcarboxyl groups, thiocarbamyl groups, groups Z, groups —CO—Z and groups —CO—OZ, wherein:

one of said $R_4$, $R'_4$, $R_5$ and $R'_5$, which may be identical or different, may optionally also be chosen from $(C_1-C_6)$alkylcarboxyl groups, $(C_1-C_6)$alkylcarbonyl groups, formyl groups, trifluoro$(C_1-C_6)$ alkylcarbonyl groups, amino$(C_1-C_6)$alkylcarbonyl groups, N—Z-amino$(C_1-C_6)$alkylcarbonyl groups, N—$(C_1-C_6)$alkylamino$(C_1-C_6)$alkylcarbonyl groups, N,N-di$(C_1-C_6)$alkylamino$(C_1-C_6)$ alkylcarbonyl groups, carbamyl groups, N—$(C_1-C_6)$ alkylcarbamyl groups, N,N-di$(C_1-C_6)$alkylcarbamyl groups, thiocarbamyl groups, aminosulphonyl groups, N—Z-aminosulphonyl groups, N—$(C_1-C_6)$ alkylaminosulphonyl groups, N,N-di$(C_1-C_6)$ alkylaminosulphonyl groups, $(C_1-C_6)$ alkylsulphonyl groups, groups —CO—Z and groups —CO—OZ;

groups Z, which may be identical or different, are each chosen from groups of formula (II):

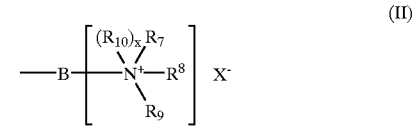

wherein:

B is a linker arm chosen from linear and branched divalent alkyl groups, which are optionally interrupted by at least one heteroatom and which are optionally substituted with at least one group chosen from hydroxyl groups and $C_1-C_6$ alkoxy groups;

$R_7$, $R_8$ and $R_9$, which may be identical or different, are each chosen from $C_1-C_6$ alkyl groups, $C_1-C_6$ monohydroxyalkyl groups, $C_2-C_6$ polyhydroxyalkyl groups, $(C_1-C_6)$alkoxy$(C_1-C_6)$alkyl groups, cyano $(C_1-C_6)$alkyl groups, aryl groups, benzyl groups, carbamyl$(C_1-C_6)$alkyl groups, N—$(C_1-C_6)$ alkylcarbamyl$(C_1-C_6)$alkyl groups, tri$(C_1-C_6)$ alkylsilane$(C_1-C_6)$alkyl groups and $C_1-C_6$ aminoalkyl groups wherein said amino group is protected with at least one group chosen from $(C_1-C_6)$alkylcarbonyl groups, carbamyl groups and $(C_1-C_6)$alkylsulphonyl groups, wherein:

two of said $R_7$, said $R_8$ and said $R_9$ may optionally form, together with the nitrogen atom to which they are attached, at least one ring comprising at least one heteroatom chosen from 5-membered saturated rings and 6-membered saturated rings, wherein said at least one ring may optionally be substituted with at least one group chosen from halogen atoms, hydroxyl groups, $C_1-C_6$ alkyl groups, $C_1-C_6$ monohydroxyalkyl groups, $C_2-C_6$ polyhydroxyalkyl groups, nitro groups, cyano groups, cyano$(C_1-C_6)$alkyl groups, $C_1-C_6$ alkoxy groups, tri($C_1$–$C_6$)alkylsilane($C_1$–$C_6$)alkyl groups, amido groups, aldehydo groups, carboxyl groups, ($C_1$–$C_6$)alkylcarbonyl groups, thio groups, $C_1$–$C_6$ thioalkyl groups, ($C_1$–$C_6$)alkylthio groups, amino groups, amino groups protected with at least one group chosen from ($C_1$–$C_6$) alkylcarbonyl groups, carbamyl groups and ($C_1$–$C_6$)alkylsulphonyl groups; and one of said $R_7$, said $R_8$ and said $R_9$ may optionally also be chosen from groups Z;

$X^-$ is chosen from monovalent anions and divalent anions;

$R_{10}$, which may be identical or different, are each chosen from $C_1$–$C_6$ alkyl groups, $C_1$–$C_6$ monohydroxyalkyl groups, $C_2$–$C_6$ polyhydroxyalkyl groups, aryl groups, benzyl groups, $C_1$–$C_6$ aminoalkyl groups, $C_1$–$C_6$ aminoalkyl group in which said amine groups is protected with at least one group chosen from ($C_1$–$C_6$)alkylcarbonyl groups, carbamyl groups and $C_1$–$C_6$ alkylsulphonyl groups, carboxy ($C_1$–$C_6$)alkyl groups, cyano($C_1$–$C_6$)alkyl groups, carbamyl($C_1$–$C_6$)alkyl groups, $C_1$–$C_6$ trifluoroalkyl groups, tri($C_1$–$C_6$)alkylsilane($C_1$–$C_6$)alkyl groups, $C_1$–$C_6$ sulphonamidoalkyl groups, ($C_1$–$C_6$) alkylcarboxy($C_1$–$C_6$)alkyl groups, ($C_1$–$C_6$) alkylsulphinyl($C_1$–$C_6$)alkyl groups, ($C_1$–$C_6$) alkylsulphonyl($C_1$–$C_6$)alkyl groups, ($C_1$–$C_6$) alkylketo($C_1$–$C_6$)alkyl groups, N—($C_1$–$C_6$) alkylcarbamyl($C_1$–$C_6$)alkyl groups and N—($C_1$–$C_6$) alkylsulphonamido($C_1$–$C_6$)alkyl groups;

x is 0 or 1, with the proviso that:
when x=0, said linker arm B is directly bonded to at least one nitrogen atom substituted with $R_7$ $R_8$ and $R_9$;

when x=1, two of said $R_7$, $R_8$ and $R_9$ form, together with the nitrogen atom to which they are attached, at least one ring comprising at least one heteroatom chosen from 5-membered saturated rings and 6-membered saturated rings, wherein said at least one ring may optionally be substituted with at least one group chosen from halogen atoms, hydroxyl groups, $C_1$–$C_6$ alkyl groups, $C_1$–$C_6$ monohydroxyalkyl groups, $C_2$–$C_6$ polyhydroxyalkyl groups, nitro groups, cyano groups, cyano ($C_1$–$C_6$)alkyl groups, $C_1$–$C_6$ alkoxy groups, tri ($C_1$–$C_6$)alkylsilane($C_1$–$C_6$)alkyl groups, amido groups, aldehydo groups, carboxyl groups, ($C_1$–$C_6$)alkylcarbonyl groups, thio groups, $C_1$–$C_6$ thioalkyl groups, ($C_1$–$C_6$)alkylthio groups, amino groups, amino groups protected with at least one group chosen ($C_1$–$C_6$)alkylcarbonyl groups, carbamyl groups and ($C_1$–$C_6$)alkylsulphonyl groups; and said linker arm B is directly bonded to at least one carbon atom of said at least one ring;

with the proviso that said monobenzenic couplers of formula (I) comprise at least one group Z; and with the further proviso that when:
said monobenzenic couplers of formula (I) comprise only one group Z, $A_1$ is chosen from groups —$NR_4R_5$ and $A_2$ is chosen from groups —$NR'_4R'_5$ *wherein*:

$R_4$ and $R_5$, which may be identical or different, are each chosen from hydrogen atoms, $C_1$–$C_6$ alkyl groups and $C_1$–$C_6$ hydroxyalkyl groups, and $R'_4$ and $R'_5$ are each chosen from hydrogen atoms; or $R_4$ and $R_5$ are each chosen from hydrogen atoms, and $R'_4$ and $R'_5$, which may be identical or different, are each chosen from hydrogen atoms, $C_1$–$C_6$ alkyl groups and $C_1$–$C_6$ hydroxyalkyl groups, and only one of said $R_1$, $R_2$ and $R_3$ is chosen from groups $OR_6$, wherein:

$R_6$ is chosen from groups Z, wherein:

said linker arm B is chosen from divalent $C_3$ alkyl groups monosubstituted in position 2 with a hydroxyl group, and said $R_7$, $R_8$ and $R_9$, which may be identical or different, are each chosen from $C_1$–$C_6$ alkyl groups and $C_1$–$C_6$ hydroxyalkyl groups or together with the nitrogen atom to which they are attached, form a ring chosen from morpholine rings and piperidine rings, then the other two of said $R_1$, $R_2$ and $R_3$ cannot simultaneously be chosen from hydrogen atoms; and with the exclusion of:

ethyl(2-hydroxyethyl)dimethylammonium 4-(methylamino) salicylate bromide;

3-[(4-amino-2-hydroxybenzoyl)oxy]-N-ethyl-N,N-dimethyl-1-propanaminium iodide;

3-[(4-amino-2-hydroxybenzoyl)oxy]-N,N,N-trimethyl-1-propanaminium iodide;

triethyl(2-hydroxyethyl)ammonium 4-aminosalicylate bromide;

2-[(4-amino-2-hydroxybenzoyl)oxy]-N,N-diethyl-N-methylethanaminium iodide;

2-[(4-amino-2-hydroxybenzoyl)oxy]-N-ethyl-N,N-dimethylethanaminium iodide;

ethyl(2-hydroxyethyl)dimethylammonium-4-aminosalicylate bromide;

2-[(4-amino-2-hydroxybenzoyl)oxy]-N,N,N-trimethylethanaminium iodide;

-2-[(4-amino-2-hydroxybenzoyl)oxy]-N,N,-trimethylethanaminium chloride;

trimethyl[(3-dipropylaminophenylcarbamoyl)methyl] ammonium chloride;

trimethyl[(3-dimethylamino-4-methoxyphenylcarbamoyl) methyl]ammonium methosulphate;

trimethyl[(3-di-b-hydroxyethylaminophenylcarbamoyl) methyl]ammonium ethosulphate;

trimethyl[(3-aminophenylcarbamoyl)methyl]ammonium iodide;

diethylmethyl[(3-aminophenylcarbamoyl)methyl] ammonium iodide;

benzyldiethyl[(3-aminophenylcarbamoyl)methyl] ammonium chloride;

trimethyl[(3,5-dihydroxyphenylcarbamoyl)ethyl] ammonium iodide;

2-[(3,5-dihydroxybenzoyl)oxy]-N,N,N-trimethylethanaminium; and

2-[(2,6-dihydroxybenzoyl)oxy]-N,N,N-trimethylethanaminium.

56. A compound according to claim 55, wherein said $X^-$ is chosen from halogen anions, hydroxide anions, hydrogen sulphate anions and $C_1$–$C_6$ alkyl sulphate anions.

57. A compound according to claim 56, wherein said halogen anions are chosen from chloride, bromide, fluoride and iodide.

58. A compound according to claim 56, wherein said $C_1$–$C_6$ alkyl sulphate anions are chosen from methyl sulphate anions and ethyl sulphate anions.

59. A compound according to claim 55, wherein said B is chosen from linear and branched divalent alkyl groups comprising from 1 to 14 carbon atoms.

60. A compound according to claim 55, wherein said at least one heteroatom is chosen from oxygen, sulphur and nitrogen.

61. A compound according to claim 55, wherein said two of said $R_7$, said $R_8$ and said $R_9$ form, together with the nitrogen atom to which they are attached, at least one ring comprising at least one heteroatom chosen from pyrrolidone rings, piperidine rings, piperazine-rings and morpholine rings.

62. A compound chosen from:

[2-(2,4-diaminophenoxy)ethyl]diethylmethylammonium chloride;
1-[3-(2,4-diaminophenoxy)propyl]-1,4-dimethylpiperazin-1-ium chloride;
1-[(3-hydroxy-4-methylphenylcarbamoyl)methyl]-1,4-dimethylpiperazin-1-ium chloride;
1,4-bis(2-hydroxyethyl)-1-[(3-hydroxyphenylcarbamoyl)methyl]piperazin-1-ium chloride;
[3-(2,4-diaminophenoxy)propyl]triethylammonium chloride;
1-[(2,4-dihydroxyphenylcarbamoyl)methyl]-1-methylpiperidinium chloride;
[2-(2,4-dihydroxyphenyl)-2-oxoethyl]triethylammonium chloride;
1-[(3-hydroxy-4-methylphenylcarbamoyl)methyl]-1-methylpyrrolidinium chloride;
1-[(2,6-dihydroxyphenylcarbamoyl)methyl]-1-methylpyrrolidinium chloride;
[2-(4-amino-2-hydroxyphenoxy)ethyl]diethylmethylammonium chloride;
triethyl[2-(3-hydroxy-4-methylphenylamino)ethyl]ammonium bromide;
1-[2-(3-hydroxy-4-methylphenylamino)ethyl]-1,4-dimethylpiperazin-1-ium bromide;
4-[(3-hydroxyphenylcarbamoyl)methyl]-4-methylmorpholin-4-ium chloride;
triethyl[2-(3-hydroxy-2,4-dimethylphenylcarbamoyloxy)ethyl]ammonium chloride;
[2-(4-chloro-3-hydroxyphenylamino)ethyl]triethylammonium bromide;
1-[3-(2-amino-4-methylaminophenoxy)propyl]-1-methylpiperidinium chloride;
[2-(2,4-diaminophenoxy)ethyl]diethylmethylammonium chloride;
1-(3-trimethylammonium-2-hydroxypropyl)-1-[(3-hydroxy-4-methylphenylcarbamoyl)methyl]pyrrolidinium dichloride;
1-[2-(3-amino4-methoxyphenylamino)ethyl]-1,4-dimethylpiperazin-1-ium bromide;
[2-(2,4-diaminophenyl)ethyl]triethylammonium chloride;
1-[(3-hydroxy-2,4-dimethylphenylcarbamoyl)methyl]-1,4-dimethylpiperazin-1-ium chloride;
N,N-bis[2-(1-methylpyrrolidinium)ethyl]benzene-1,3-diamine dichloride;
triethyl-[(3-hydroxy-4-methylphenylcarbamoyl)methyl]ammonium chloride;
N,N'-bis{2-[1,4-bis(2-hydroxyethyl)piperazin-1-ium]ethyl}benzene-1,3-diamine-2-methyl dichloride;
1-[3-(2,4-diaminophenoxy)propyl]-1-methylpyrrolidinium chloride;
1-[(3-hydroxyphenylcarbamoyl)methyl]-1,4-dimethylpiperazin-1-ium chloride;
1-[3-(2,4-diaminophenoxy)propyl]-4-(3-trimethylammonium-2-hydroxypropyl)-1,4-dimethylpiperazine-1,4-diium trichloride; or an acid addition salt of any of the foregoing said compounds.

* * * * *

UNITED STATES PATENT AND TRADEMARK OFFICE
CERTIFICATE OF CORRECTION

PATENT NO. : 6,419,711 B1
DATED : July 16, 2002
INVENTOR(S) : Alain Genet and Alain Lagrange It is certified that error appears in the above-identified patent and that said Letters Patent is hereby corrected as shown below:

<u>Title page,</u>
Item "[22] Filed: Nov. 13, 2000" should read
--   [22]   PCT Filed:       Mar. 15, 1999
     [86]   PCT No.:        PCT/FR99/00574
            § 371 date:       Nov. 13, 2000
            § 102(e) date:    Nov. 13, 2000
   [87]   PCT Publ. No.:   WO 99/48856
            PCT Publ. Date:  Sep. 30, 1999 --.

<u>Column 22,</u>
Lines 14-15, "amino($C_1$-$C_8$)alkylcarbonyl" should read -- amino($C_1$-$C_6$)alkylcarbonyl --.
Lines 63-64, "N-($C_{1-6}$)alkylcarbamyl($C_1$-$C_6$)alkyl" should read -- N-($C_1$-$C_6$)alkylcarbamyl($C_1$-$C_6$)alkyl --.

<u>Column 23,</u>
Line 19, "-NR'$_4$R'," should read -- NR'$_4$R'$_5$ --.

<u>Column 24,</u>
In the structure for formula (II) at the top,

"
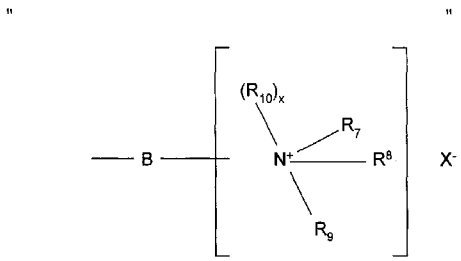
"

should read

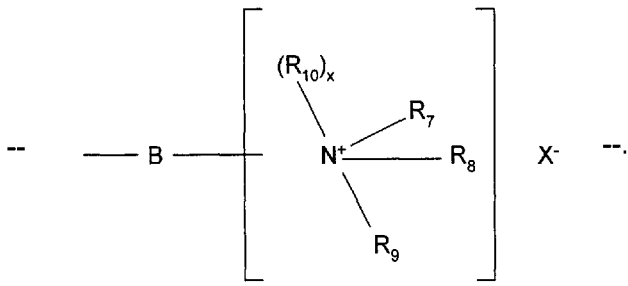

UNITED STATES PATENT AND TRADEMARK OFFICE
CERTIFICATE OF CORRECTION

PATENT NO.    : 6,419,711 B1
DATED         : July 16, 2002
INVENTOR(S)   : Alain Genet and Alain Lagrange It is certified that error appears in the above-identified patent and that said Letters Patent is hereby corrected as shown below:

Column 25,
Line 20, after "group chosen", insert -- from --.
Line 30, "-NR'$_4$R'$_{5\ wherein:}$" should read -- -NR'$_4$R'$_5$ wherein: --.

Column 28,
Line 44, "according claim 1," should read -- according to claim 1, --.

Column 30,
Line 33, "N-($C_1$-$C_6$)alkylamihosulphonyl($C_1$-$C_6$)alkyl" should read -- N-($C_1$-$C_6$)alkylaminosulphonyl($C_1$-$C_6$)alkyl --.
Line 43, "OR$_6$," should read -- OR$_6$, --.

Column 32,
In the structure for formula (II) after line 5,

"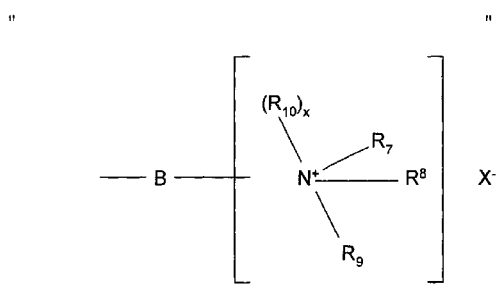"

should read

-- 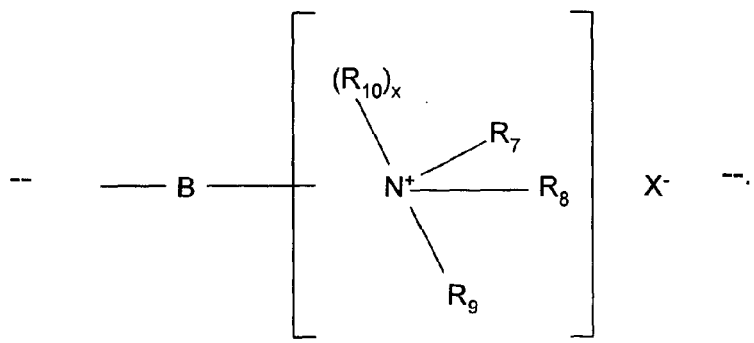 --.

Line 67, "($C_{C6}$)alkylsulphonyl($C_1$-$C_6$)alkyl" should read -- ($C_1$-$C_6$)alkylsulphonyl($C_1$-$C_6$)alkyl --.

UNITED STATES PATENT AND TRADEMARK OFFICE
CERTIFICATE OF CORRECTION

PATENT NO.  : 6,419,711 B1
DATED       : July 16, 2002
INVENTOR(S) : Alain Genet and Alain Lagrange It is certified that error appears in the above-identified patent and that said Letters Patent is hereby corrected as shown below:

Column 33,
Line 34, "A2" should read -- $A_2$ --.

Column 34,
Line 28, "are choen" should read -- are chosen --.

Column 36,
In the structure for formula (II) after line 41,

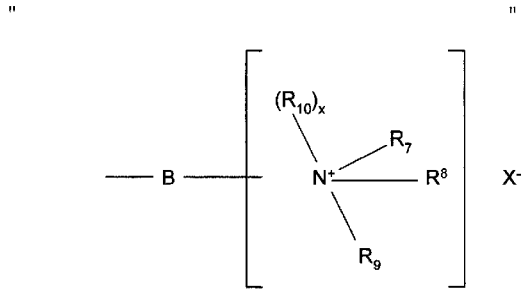

should read

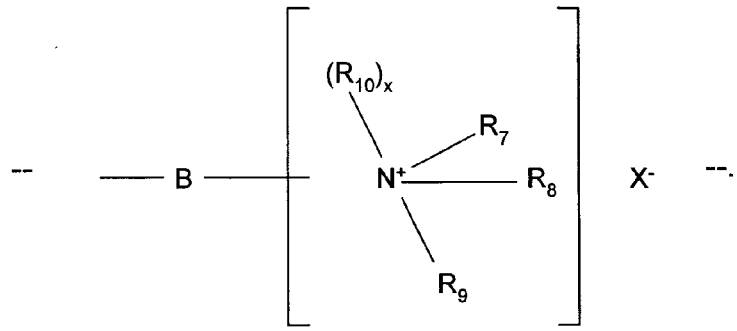

Lines 59-60, "cyano($C_1$-$C_8$)alkyl" should read -- cyano($C_1$-$C_6$)alkyl --.

Column 37,
Line 33, "tri($C_1$-$C_6$)alkylsilane($C_1C_6$)alkyl" should read -- tri($C_1$-$C_6$)alkylsilane($C_1$-$C_6$)alkyl --.

Column 38,
Line 3, "A2" should read -- $A_2$ --.
Line 5, "$R_4$and" should read -- $R_4$ and --.
Line 25, "atoms" should read -- atoms; --.

UNITED STATES PATENT AND TRADEMARK OFFICE
CERTIFICATE OF CORRECTION

PATENT NO. : 6,419,711 B1
DATED : July 16, 2002
INVENTOR(S) : Alain Genet and Alain Lagrange It is certified that error appears in the above-identified patent and that said Letters Patent is hereby corrected as shown below:

<u>Column 39,</u>
Line 45, "thiocrbamyl" should read -- thiocarbamyl --.

<u>Column 40,</u>
In the structure for formula (II) after line 30,

"                                                                    "

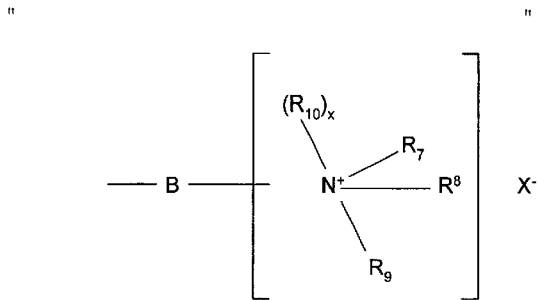

should read

-- 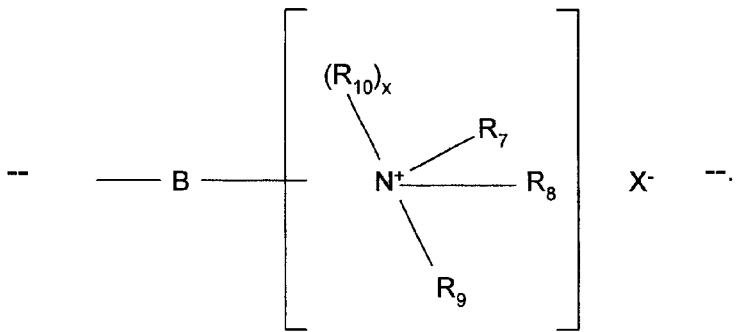 --.

<u>Column 41,</u>
Line 18, "groups is protected" should read -- group is protected --.
Line 33, "$R_7 R_8$" should read -- $R_7, R_8$ --.
Line 51, after "group chosen", insert -- from --.
Line 61, "-NR'$_4$R'$_5$ $_{wherein:}$" should read -- -NR'$_4$R'$_5$ wherein: --.

UNITED STATES PATENT AND TRADEMARK OFFICE
CERTIFICATE OF CORRECTION

PATENT NO. : 6,419,711 B1
DATED : July 16, 2002
INVENTOR(S) : Alain Genet and Alain Lagrange It is certified that error appears in the above-identified patent and that said Letters Patent is hereby corrected as shown below:

Column 42,
Line 34, "-2-[(4-amino-2-hydroxybenzoyl)oxy]-N,N,-" should read
-- 2-[(4-amino-2-hydroxybenzoyl)oxy]-N,N,N- --.

Column 44,
Line 12, "1-[2-(3-amino4-methoxyphenylamino)ethyl-1,4-" should read
-- 1-[2-(3-amino-4-methoxyphenylamino)ethyl-1,4- --.

Signed and Sealed this

Seventeenth Day of December, 2002

JAMES E. ROGAN
*Director of the United States Patent and Trademark Office*